US008980285B2

(12) United States Patent
Granoff et al.

(10) Patent No.: US 8,980,285 B2
(45) Date of Patent: *Mar. 17, 2015

(54) **VACCINES FOR BROAD SPECTRUM PROTECTION AGAINST *NEISSERIA MENINGITIDIS***

(75) Inventors: Dan M. Granoff, Berkeley, CA (US); Gregory R. Moe, Alameda, CA (US)

(73) Assignee: Children's Hospital & Research Center At Oakland, Oakland, CA (US)

( * ) Notice: Subject to any disclaimer, the term of this patent is extended or adjusted under 35 U.S.C. 154(b) by 1353 days.

This patent is subject to a terminal disclaimer.

(21) Appl. No.: 11/081,882

(22) Filed: Mar. 15, 2005

(65) Prior Publication Data

US 2006/0029621 A1 Feb. 9, 2006

Related U.S. Application Data

(63) Continuation of application No. 09/917,222, filed on Jul. 27, 2001, now Pat. No. 6,936,261.

(60) Provisional application No. 60/221,495, filed on Jul. 27, 2000.

(51) Int. Cl.
A61K 39/095 (2006.01)
A61K 45/06 (2006.01)
A61K 31/56 (2006.01)
A61K 39/00 (2006.01)

(52) U.S. Cl.
CPC ............... *A61K 45/06* (2013.01); *A61K 31/56* (2013.01); *A61K 39/095* (2013.01); *A61K 2039/55555* (2013.01)
USPC .................................................. 424/249.1

(58) Field of Classification Search
None
See application file for complete search history.

(56) References Cited

U.S. PATENT DOCUMENTS

| 4,601,903 | A | 7/1986 | Frasch |
| 4,727,136 | A | 2/1988 | Jennings et al. |
| 5,597,572 | A | 1/1997 | Huergo et al. |
| 5,705,161 | A | 1/1998 | Van Der Ley et al. |
| 5,747,653 | A | 5/1998 | Huergo et al. |
| 6,180,111 | B1 | 1/2001 | Stein et al. |
| 6,482,807 | B1 | 11/2002 | Van Der Ley et al. |
| 6,936,261 | B2 | 8/2005 | Granoff et al. |
| 2002/0110569 | A1 | 8/2002 | Granoff et al. |
| 2003/0021812 | A1 | 1/2003 | Robinson et al. |
| 2003/0215469 | A1 | 11/2003 | Robinson et al. |
| 2004/0126389 | A1 | 7/2004 | Berthet et al. |
| 2006/0171957 | A1 | 8/2006 | Pizza |
| 2006/0216307 | A1 | 9/2006 | Berthet et al. |
| 2006/0240045 | A1 | 10/2006 | Berthet et al. |
| 2006/0251670 | A1 | 11/2006 | Comanducci et al. |
| 2008/0248065 | A1 | 10/2008 | Granoff et al. |
| 2009/0035328 | A1 | 2/2009 | Granoff et al. |

FOREIGN PATENT DOCUMENTS

| EP | 0 449 958 B1 | 3/1995 |
| EP | 1208214 | 11/2006 |
| WO | WO9006696 | 6/1990 |
| WO | WO 96/29412 | 9/1996 |
| WO | WO 98/02547 | 1/1998 |
| WO | WO 98/56901 | 12/1998 |
| WO | WO 99/57280 | 4/1999 |
| WO | WO 99/24578 | 5/1999 |
| WO | WO 99/36544 | 7/1999 |
| WO | WO 99/61053 | 12/1999 |
| WO | WO 00/66791 | 2/2000 |
| WO | WO 00/22430 | 4/2000 |
| WO | WO0025811 A2 | 5/2000 |
| WO | WO 0026384 | 5/2000 |
| WO | WO 01/09350 | 2/2001 |
| WO | WO 01/34642 A2 | 5/2001 |
| WO | WO 01/37863 A2 | 5/2001 |
| WO | WO 0152885 | 7/2001 |
| WO | WO 0191788 | 12/2001 |
| WO | WO 0228888 | 4/2002 |
| WO | WO 02062378 | 8/2002 |
| WO | WO 02062380 | 8/2002 |
| WO | WO 03010194 | 2/2003 |
| WO | WO 03051379 | 6/2003 |
| WO | WO 03105890 | 12/2003 |
| WO | WO 2004002523 | 1/2004 |
| WO | WO 2004014417 | 2/2004 |
| WO | WO 2004014418 | 2/2004 |
| WO | WO 2004014419 | 2/2004 |
| WO | WO 2004015099 | 2/2004 |
| WO | WO 2004019977 | 3/2004 |
| WO | WO 2004048404 | 6/2004 |

OTHER PUBLICATIONS

Greenspan et al. (Nature Biotechnology 7: 936-937, 1999).*
Beernink, et al. "Prevalence of factor H-binding protein variants and NadA among meningococcal group B isolates from the United States: implications for the development of a multicomponent group B vaccine" *J Infect Dis* 2007;195:1472-1479.
Bjune, et al, Effect of outer membrane vesicle vaccine against group B meningococcal disease in Norway. *Lancet* 1991;338:1093-6.
Fukasawa, L. O., et al. Immune response to native NadA from *Neisseria meningitidis* and its expression in clinical isolates in Brazil. *J. Med. Microbiol.* 2003, vol. 52, pp. 121-125.
Giuliani, et al, A universal vaccine for serogroup B meningococcus. *Proc Natl Acad Sci U S A* 2006;103:10834-9.
Hou, et al. "Protective antibody responses elicited by a meningococcal outer membrane vesicle vaccine with overexpressed genome-derived neisserial antigen 1870" *J. Infect. Dis.* 2005;192:580-90 (Epub Jul. 15, 2005).
Koeberling, et al. Improved immunogenicity of a H44/76 group B outer membrane vesicle vaccine with over-expressed genome-derived Neisserial antigen 1870. Vaccine 2007;25:1912-20 (Epub Apr. 21, 2006).

(Continued)

Primary Examiner — Robert A Zeman
(74) Attorney, Agent, or Firm — Bozicevic, Field & Francis LLP; Paula A. Borden

(57) ABSTRACT

The present invention generally provides methods and vaccines for the prevention of diseases caused by *Neisseria meningitidis* bacteria, particularly serogroup B strains.

7 Claims, 23 Drawing Sheets

(56) References Cited

OTHER PUBLICATIONS

Figure 2:
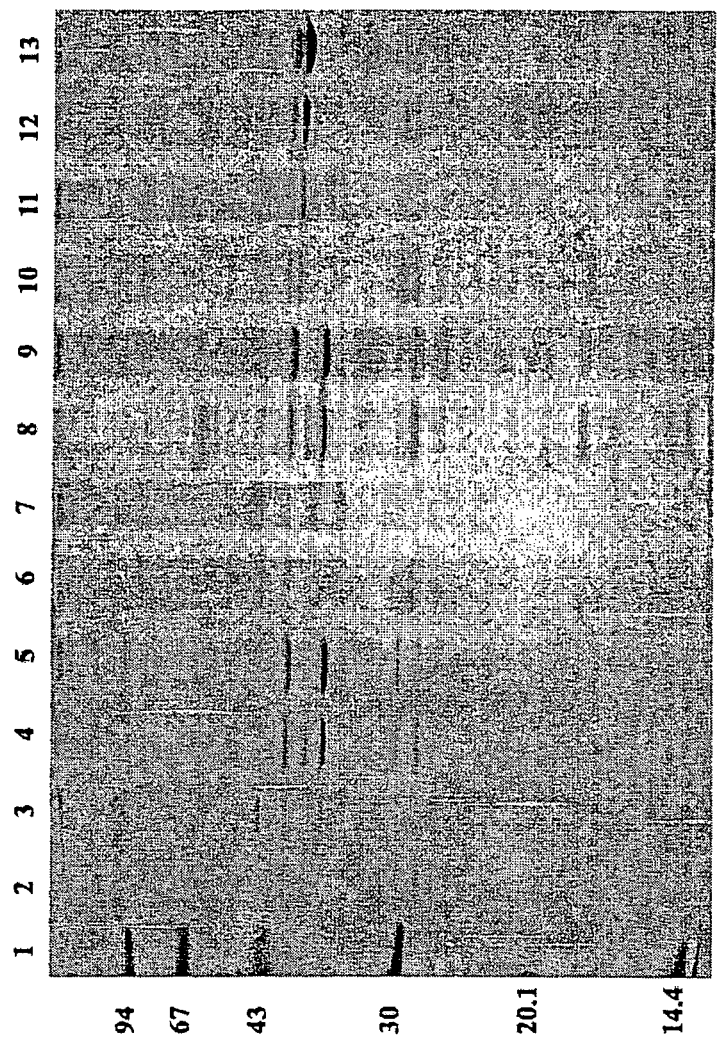

Koeberling, et al. Bactericidal antibody responses elicited by a meningococcal outer membrane vesicle vaccine with overexpressed factor H-binding protein and genetically attenuated endotoxin. J Infect Dis. Jul. 15, 2008;198(2):262-70.

Koeberling, et al. Meningococcal outer membrane vesicle vaccines derived from mutant strains engineered to express factor H binding proteins from antigenic variant groups 1 and 2. Clin Vaccine Immunol. Feb. 2009;16(2):156-62.

Masignani, et al, Vaccination against Neisseria meningitidis using three variants of the lipoprotein GNA1870. J Exp Med 2003;197(6):789-99.

O'Dwyer, et al, Expression of heterologous antigens in commensal Neisseria spp.: preservation of conformational epitopes with vaccine potential. Infect Immun 2004;72(11):6511-6518.

Pillai, et al. (2005) "Outer Membrane Protein (OMP) based Vaccine for Neisseria meningitidis Serogroup B" Vaccine 23(17-18):2206-2209.

Unemo, et al. (2005) "The porA pseudogene of Neisseria gonorrhoeae—low level of genetic polymorphism and a few, mainly identical, inactivating mutations" APMIS 113(6):410-419.

Welsch, et al, Protective activity of monoclonal antibodies to genome-derived neisserial) antigen 1870, a Neisseria meningitidis candidate vaccine. J Immunol 2004;172:5606-15.

Van Der Voort, et al., "Human B and T-Cell Responses After Immunization with a Hexavalent PorA Meningococcal Outer Membranes Vesicle Vaccine," Infection and Immunity, 1997, vol. 65, No. 12, pp. 5184-5190.

Van Der Voort, et al., "Immunogenicity Studies with a Genetically Engineered Hexavalent PorA and a Wild-Type Meningococcal Group B Outer Membrane Vesicle Vaccine in Infant Cynomolgus Monkeys", Vaccine, 2000, vol. 18, pp. 1334-1343.

Baker, M. G., et al. A 10 year serogroup B meningococcal disease epidemic in New Zealand: descriptive epidemiology, 1991-2000. J Paediatr Child Health. 2001, vol. 37, pp. S13-S19.

Beernink & Granoff (2008) "Bactericidal antibody responses induced by meningococcal recombinant chimeric factor H-binding protein vaccines" Infect. Immun. 76(6):2568-2575.

Beernink et al, Rapid genetic grouping of factor h-binding protein (genome-derived neisserial antigen 1870), a promising group B meningococcal vaccine candidate. Clin Vaccine Immunol 2006;13:758-63.

Bjerre et al, Complement activation induced by purified Neisseria meningitidis lipopolysaccharide (LPS), outer membrane vesicles, whole bacteria, and an LPS-free mutant. J Infect Dis 2002;185:220-8.

Bjune (1991) "Results of an efficacy trial with an outer membrane vesicle vaccine against systemic serogroup B meningococcal disease in Norway" NIPH Ann. 14(2):125-130.

Bonvehi et al. Three doses of an experimental detoxified L3-derived lipooligosaccharide meningococcal vaccine offer good safety but low immunogenicity in healthy young adults. Clin. Vaccine Immunol., Jul. 21, 2010 doi:10.1128/CVI.00129-10.

Borrow et al, Neisseria meningitidis group B correlates of protection and assay standardization—international meeting report Emory University, Atlanta, Georgia, United States, Mar. 16-17, 2005. Vaccine 2006;24:5093-107.

Braun et al, Proinflammatory responses to lipo-oligosaccharide of Neisseria meningitidis immunotype strains in relation to virulence and disease. J Infect Dis 2002;185:1431-8.

Cantini et al, Solution structure of the immunodominant domain of protective antigen GNA1870 of Neisseria meningetidis. J Biol Chem 2006;281:7220-7 (Epub Dec. 31, 2005).

Cartwright, K., et al. Meningococcal disease in Europe: epidemiology, mortality, and prevention with conjugate vaccines. Report of a European advisory board meeting in Vienna, Austria, Oct. 6-8, 2000. Vaccine. 2001, vol. 19, pp. 4347-4356.

Christodoulides, M., et al. Immunization with recombinant class 1 outer-membrane protein from Neisseria meningitidis: influence of liposomes and adjuvants on antibody avidity, recognition of a native protein and the induction of a bactericidal immune response against meningococci. Microbiology. 1998. vol. 144, pp. 3027-3037.

Claassen et al, Production, characterization, and control of a Neisseria meningitides hexavalent class 1 outer membrane protein containing a vesicle vaccine. Vaccine 1996;14(10):1001-8.

De Groot, A. S., et al. Genome derived vaccines. Expert Rev Vaccines. 2004, vol. 3, pp. 59-76.

Desmond, N., et al. Getting to grips with an epidemic. Nurs N Z. 2004, vol. 10, p. 2.

Devoe et al, Release of endotoxin in the form of cell wall blebs during in vitro growth of Neisseria meningitidis. J Exp Med 1973;138:1156-67.

Ferrari et al, Outer membrane vesicles from group B Neisseria meningitidis Deltagna33 mutant: Proteomic and immunological comparison with detergent-derived outer membrane vesicles. Proteomics 2006;6:1856-66.

Findlow et al, Comparison and correlation of Neisseria meningitidis serogroup B immunologic assay results and human antibody responses following three doses of the Norwegian meningococcal outer membrane vesicle vaccine MenBvac. Infect Immun 2006;74:4557-65.

Finne, J., et al. Antigenic similarities between brain components and bacteria causing meningitidis. Implications for vaccine development and pathogenesis. Lancet. 1983, vol. 2, pp. 355-357.

Fisseha et al, Characterization of Native Outer Membrane Vesicles from lpxL Mutant Strains of Neisseria meningitidis for Use in Parenteral Vaccination. Infect Immun 2005;73(7):4070-80.

Fisseha et al, Characterization of NOMV prepared from lpxL1 and lpxL2 mutants of Neisseria meningitidis with L3,7 and L8 lipooligosaccharide. Thirteen international Pathogenic Neisseria Conference Nordberg Aksidenstrykkeri, 2002.

Fletcher et al, Vaccine potential of the Neisseria meningitidis 2086 lipoprotein. Infect Immun 2004;72(4):2088-100.

Frasch et al, Meningococcal vaccines: methods and protocols. Totowa, New Jersey: Humana Press, 2001:81-107.

Fukasawa et al, Adjuvant can improve protection induced by OMV vaccine against Neisseria meningitidis serogroups B/C in neonatal mice. FEMS Immunol Med Microbiol 2004;41:205-10.

Giuliani et al, A universal vaccine for serogroup B Meningococcus. In: 15th International Pathogenic Neisseria Conference. Cairns, Australia, 2006.

Giuliani et al, The region comprising amino acids 100 to 255 of Neisseria meningitidis lipoprotein GNA 1870 elicits bactericidal antibodies. Infect Immun 2005;73:1151-60.

Gonzalez et al, Immunization with Neisseria meningitidis outer membrane vesicles prevents bacteremia in neonatal mice. Vaccine 2006;24:1633-43.

Granoff, D., et al. Meningococcal Vaccines. In: Vaccines $4^{th}$ ed., Plotkin, S.A. and Orenstein, W. A., eds. Philadelphia: W.B. Saunders Company, 2003:959-987.

Granoff, et al. (2001) "A novel mimetic antigen eliciting protective antibody to Neisseria meningitidis" J. Immunol. 167(11):6487-6496.

Gunn, et al. (1998) "PmrA-PmrB-regulated genes necessary for 4-aminoarabinose lipid A modification and polymyxin resistance" Mol. Microbiol. 27:1171-1182.

Holst et al, The concept of "tailor-made", protein-based, outer membrane vesicle vaccines against meningococcal disease. Vaccine 2005;23:2202-5.

Holst, et al. (2003) "Serum bactericidal activity correlates with the vaccine efficacy of outer membrane vesicle vaccines against Neisseria meningitidis serogroup B disease" Vaccine 21(78):734-737.

Hou, et al. (2003) "Conformational epitopes recognized by protective anti-neisserial surface protein A antibodies" Infect. Immun. 71(12):6844-6849.

Humphries, H.E., et al. Recombinant meningococcal PorA protein, expressed using a vector system with potential for human vaccination, induces a bactericidal immune response. Vaccine. 2004, vol. 22, pp. 1564-1569.

Jacobsson et al, Sequence constancies and variations in genes encoding three new meningococcal vaccine candidate antigens. Vaccine 2006;24:2161-8.

(56) References Cited

OTHER PUBLICATIONS

Jansen, C., et al. Immunogenicity of in vitro folded outer membrane protein PorA of *Neisseria meningitidis*. FEMS Immunol Med Microbiol. 2000, vol. 27, pp. 227-233.

Jennings, H. J., et al. Immunochemistry of groups A, B, and C meningococcal polysaccharide-tetanus toxoid conjugates. J Immunol. 1981, vol. 127, pp. 1011-1018.

Jessouroun et al, Outer membrane vesicles (OMVs) and detoxified lipooligosaccharide (dLOS) obtained from Brazilian prevalent *N. meningitidis* serogroup B strains protect mice against homologous and heterologous meningococcal infection and septic shock. Vaccine 2004;22:2617-25.

Jodar, L., et al. Development of vaccines against meningococcal disease. Lancet. 2002, vol. 359, pp. 1499-1508.

Kahler et al, Genetic basis for biosynthesis, structure, and function of meningococcal lipooligosaccharide (endotoxin). Crit Rev Microbiol 1998;24:281-334.

Keiser et al. A phase 1 study of a meningococcal native outer membrane vesicle vaccine made from a group B strain with deleted lpxL1 and synX, over-expressed factor H binding protein, two PorAs and stabilized OpcA expression. Vaccine (2011) doi:10.1016/j.vaccine. 2010.12.039, in press.

Kijek, T., et al. Characterization of genetically detoxified native outer membrane vesicle (NOMV) vaccine prepared for human use. Thirteenth International Pathogenic *Neisseria* Conference. Norwegian Institute of Public Health, Oslo, Norway; Sep. 1-6, 2002. (Please see Abstracts of the Thirteenth International Pathogenic *Neisseria* Conference, p. 267).

Lingappa, J. R., et al. Surveillance for meningococcal disease and strategies for use of conjugate meningococcal vaccines in the United States. Vaccine. 2001, vol. 19, pp. 4566-4575.

Luijkx et al, Relative immunogenicity of PorA subtypes in a multivalent *Neisseria meningitidis* vaccine is not dependent on presentation form. Infect Immun 2003;71:6367-71.

Madico et al, The meningococcal vaccine candidate GNA1870 binds the complement regulatory protein factor H and enhances serum resistance. J Immunol 2006;177:501-10.

Martin, D., et al. Recombinant NspA incorporated into liposomal vesicles induces functional antibodies. Thirteenth International Pathogenic *Neisseria* Conference. Norwegian Institute of Public Health, Oslo, Norway; Sep. 1-6, 2002. (Please see Abstracts of the Thirteenth International Pathogenic *Neisseria* Conference, p. 134).

McGuinness, S., et al. Point mutation in meningococcal PorA gene associated with increased endemic disease. Lancet. 1991, vol. 337, pp. 514-517.

Mirlashari et al, Outer membrane vesicles from *Neisseria meningitidis*: effects on tissue factor and plasminogen activator inhibitor-2 production in human monocytes. Thromb Res 2001;102:375-80.

Mirlashari et al, Outer membrane vesicles from *Neisseria meningitidis*: effects on cytokine production in human whole blood. Cytokine 2001;13:91-7.

Moe, G. R., et al. Sequential Immunization with vesicles prepared from heterologous *Neisseria meningitidis* strains elicits broadly protective serum antibodies to group B strains. Infection and Immunity. 2002, vol. 70, pp. 6021-6031.

Morley et al. Vaccine prevention of meningococcal disease, coming soon? Vaccine 2001;20:666-87.

Mukhopadhyay et al, Rapid characterization of outer-membrane proteins in *Neisseria lactamica* by SELDI-TOF-MS (surface-enhanced laser desorption ionization-time-of-flight MS) for use in a meningococcal vaccine. Biotechnol Appl Biochem 2005;41:175-82.

Muttilainen, S., et al. The *Neisseria meningitidis* outer membrane protein P1 produced in *Bacillus subtilis* and reconstituted into phospholipid vesicles elicits antibodies to native P1 epitopes. Microb Pathog. 1995, vol. 18, pp. 423-436.

Newcombe et al, Infection with an avirulent phoP mutant of *Neisseria meningitidis* confers broad cross-reactive immunity. Infect Immun 2004;72:338-44.

Nøkleby, et al. (2007) "Safety review: two outer membrane vesicle (OMV) vaccines against systemic *Neisseria meningitidis* serogroup B disease" Vaccine 25(16):3080-3084.

Oliver, K. J., et al. *Neisseria lactamica* protects against experimental meningococcal infection. Infection and Immunity. 2002, vol. 70, pp. 3621-3626.

Parmar et al, Incorporation of bacterial membrane proteins into liposomes: factors influencing protein reconstitution. Biochim Biophys Acta 1999;1421:77-90.

Peeters et al, Immunogenicity of various presentation forms of PorA outer membrane protein of *Neisseria meningititidis* in mice. Vaccine 1999;17:2702-12.

Peeters et al, Phase I clinical trial with a hexavalent PorA containing meningococcal outer membrane vesicle vaccine. Vaccine 1996;14:1009-15.

Perrett et al, Towards an improved serogroup B *Neisseria meningitidis* vaccine. Expert Opin Biol Ther 2005;5:1611-25.

Petrov et al, Toxicity and immunogenicity of *Neisseria meningitidis* lipopolysaccharide incorporated into liposomes. Infect Immun 1992;60:3897-903.

Post et al., Biochemical and functional characterization of membrane blebs purified from *Neisseria meningitidis* serogroup B. J Biol Chem 2005;280:38383-94.

Raghunathan, P. L., et al. Opportunities for control of meningococcal disease in the United States. Annu Rev Med. 2004, vol. 55, pp. 333-353.

Rosenstein, N. E., et al. The changing epidemiology of meningococcal disease in the United States, 1992-1996. Journal of Infectious Disease. 1999, vol. 180, pp. 1894-1901.

Russell, J. E., et al. PorA variable regions of *Neisseria meningitidis*. Emerging Infectious Diseases. 2004, vol. 10, No. 4, pp. 674-678.

Sanchez, S., et al. Interspecific Neisserial high molecular weight proteins able to induce natural immunity responses are strongly correlated with no vitro bactericidal activity. Vaccine. 2002, vol. 20, pp. 2964-2971.

Sandbu, et al. (2007) "Immunogenicity and safety of a combination of two serogroup B meningococcal outer membrane vesicle vaccines" *Clin. Vaccine Immunol.* 14(9):1062-1069.

Saunders et al, Immunogenicity of intranasally administered meningococcal native outer membrane vesicles in mice. Infect. and Immun. 1999;67:113-119.

Steeghs et al, Meningitis bacterium is viable without endotoxin. Nature 1998;392:449-50.

Steeghs et al, Outer membrane composition of a lipopolysaccharide-deficient *Neisseria meningitidis* mutant. EMBO J 2001;20:6937-45.

Steeghs et al, Teasing apart structural determinants of 'toxicity' and 'adjuvanticity': implications for meningococcal vaccine development. J Endotoxin Res 2004;10:113-9.

Steeghs et al. Differential activation of human and mouse Toll-like receptor 4 by the adjuvant candidate LpxL1 of *Neisseria meningitidis*. Infection and Immunity, Aug. 2008, p. 3801-3807.

Steeghs, et al. (1999) "Immunogenicity of outer membrane proteins in a lipopolysaccharide-deficient mutant of *Neisseria meningitidis*: influence of adjuvants on the immune response" *Infect. Immun.* 67(10):4988-4993.

Taha et al, Use of available outer membrane vesicle vaccines to control serogroup B meningococcal outbreaks. Vaccine 2007;25:2537-8.

Thomas, M., et al. Prevention of group B meningococcal disease by vaccination: a difficult task. N Z Med J. 2004, vol. 117, p. U1016.

Troncoso, G., et al. Antigenic cross-reactivity between outer-membrane proteins of *Neisseria meningitidis* and commensal *Neisseria* species. FEMS Immunol Med Microbiol. 2000, vol. 27, pp. 103-109.

Trotter, C.L., et al. Effectiveness of meningococcal serogroup C conjugate vaccine 4 years after introduction. Lancet. 2004, vol. 364, pp. 365-367.

Tzeng et al, Endotoxin of *Neisseria meningitidis* composed only of intact lipid A: inactivation of the meningococcal 3-deoxy-D-manno-octulosonic acid transferase. J Bacteriol 2002;184:2379-88.

Van Der Ley, et al. (2001) "Modification of lipid A biosynthesis in *Neisseria meningitidis* lpxL mutants: influence on lipopolysaccharide structure, toxicity, and adjuvant activity" *Infect. Immun.* 69(10):5981-5990.

(56) References Cited

OTHER PUBLICATIONS

Van Der Ley, et al. "Construction of *Neisseria meningitidis* strains carrying multiple chromosomal copies of the porA gene for use in the production of a multivalent outer membrane vesicle vaccine" Vaccine. 1995, vol. 13, No. 4, pp. 401-407.
Vandeputte-Rutten, L., et al. Crystal structure of Neisserial surface protein A (NspA), a conserved outer membrane protein with vaccine potential. Journal of Biological Chemistry. 2003, vol. 278, pp. 24825-24830.
Vipond et al, Proteomic analysis of a meningococcal outer membrane vesicle vaccine prepared from the group B strain NZ98/254. Proteomics 2006;6:3400-13.
Welsch, et al. (2003) "Antibody to genome-derived neisserial antigen 2132, a *Neisseria meningitidis* candidate vaccine, confers protection against bacteremia in the absence of complement-mediated bactericidal activity" *J. Infect. Dis.* 188(11):1730-1740.
Welsch, et al. (2008) "Complement-dependent synergistic bactericidal activity of antibodies against factor H-binding protein, a sparsely distributed meningococcal vaccine antigen" *J. Infect. Dis.* 197(7):1053-1061.
Jones, D.M., "Current and Future Trends in Immunization Against Meningitis, Journal of Antimicrobial Chemotherapy", 1993, vol. 31, Suppl. B, pp. 93-99.
Milagres, L.G., "Antibody Studies in Mice of Outer Membrane Antigens for Use in an Improved Meningococcal B and C Vaccine", FEMS Immunology and Medical Microbiology, 1996, vol. 13, p. 9-17.
Drabick et al., "Safety and immunogenicity testing of an intranasal group B meningococcal native outer membrane vesicle vaccine in healthy volunteers", Vaccine, Aug. 20, 2000, vol. 18, Issues 1-2, pp. 160-172.
Ashton, F. E. et al., 1938, "A New Serogroup (L) of *Neisseria meningitdis*", *J. Clin. Microbiol.* 17: 722-727.
Artenstein MS, et al, "Prevention of meningococcal disease by group C polysaccharide vaccine." N Engl J Med 1970;282:417-20.
Borrow, et al., 2001, "Serological Basis for Usse of Meningococcal Serogroup C Conjugate Vaccines in the U.K.:Reevaluation of Correlates of Protection", Infection and Immunity, 69(3):1568-1573.
Branham, S. E., 1956, "Milestones in the History of Meningococgus", Canadian Journal of Microbiology, 2:175-188.
Balmer P, et al, "Serologic correlates of protection for evaluating the response to meningococcal vaccines," Expert Rev Vaccines 2004;3:77-87.
Borrow R, et al, "Serological basis for use of meningococcal serogroup C conjugate vaccines in the United Kingdom: reevaluation of correlates of protection," Infect Immun 2001;69:1568-73.
Campagne et al. 2000, "Safety and immunogenicity of three doses of a *Neisseria* meningitides A + C diphtheria conjugate vaccine in infants from Niger", *Pediatric Infectious Disease Journal*, 19(2):144-150.
Cartwright K et al, 1999, "Immunogenicity and reactogenicity in UK infants of a novel meningococcal vesicle vaccine containing multiple class 1 (PorA) outer membrane proteins", *Vaccine*, 17:2612-2619.
De Kleinjn ED et al, 2000, "Immunogenicity and safety of a hexavalent meningococcal outermembrane-vesicle vaccine in children of 2-3 and 7-8 years of age", *Vaccine*, 18:1456-1466.
Densen P., 1989 "Interaction of complement with *Neisseria meningitidis* and *Neisseria gonorrhoeae*," Clin Microbiol, Rev;2 Suppl:S11-7.
De Wals P, et al, "Effectiveness of a mass immunization campaign against serogroup C meningococcal disease in Quebec," Jama 2001;285:177-81.
Devi S. J. et al, 1996 Binding diversity of monoclonal antibodies to alpha(2—>8) polysialic acid conjugated to outer membrane vesicle via adipic acid dihydrazide. FEMS Immunol Med Microbiol. Jul. 1996;14(4):211-20.
Frasch, C. E. and Chapman, 1973, "Classification of *Neisseria meningitidis* Group B into Distinct Serotypes. III. Application of a New Bactericidal-Inhibition Technique to Distribution of Serotypes among Cases and Carriers" *Journal of Infectious Disease*, 127:149-154.
Fusco et al., 1997, "Preclinical Evaluation of a Novel Group B Meningococcal Conjugate Vaccine that Elicits Bactericidal Activity in both Mice and Nonhuman Primates", *Journal of Infectious Diseases*, 175: 364-372.
Figueroa JE, et al, "Infectious diseases associated with complement deficiencies," Clin Microbiol Rev 1991;4:359-95.
Fijen CA, et al, "Complement deficiencies in patients over ten years old with meningococcal disease due to uncommon serogroups," Lancet 1989;2:585-8.
Frasch CE. "Meningococcal Vaccines: Past, Present and Future," In: Cartwright K, ed. Meningococcal Disease. New York: John Wiley & Sons, 1995:245-83.
Gold R, et al, "Meningococcal infections. 2. Field trial of group C meningococcal polysaccharide vaccine in 1969-70," Bull World Health Organ 1971;45:279-82.
Goldschneider I, et al, "Human immunity to the meningococcus. II. Development of natural immunity," J Exp Med 1969;129:1327-48.
Gold et al., 1969-1970, "Meningococcal Infections" *Bull. WHO*, 45: 272-282.
Goldschneider et al, 1969, "Human Immunity to the Meningococcus: I. The Role of the Humoral Antibodies" *J. Exp. Med.* 129:1307-1326.
Gotschlich et al., 1969, "Human Immunity to the Meningococcus: III. Preparation and Immunochemical Properties of the Group A, Group B, and Group C Meningococcal Polysaccharides", *J. Exp. Med.* 129:134-136.
Granoff et al., 1998, "Bacterial Monoclonal Antibodies That Define Unique Meningococcal B Polysaccharide Epitopes That Do Not Cross-React with Human Polysialic Acid", *J. Immunol*; 160: 5028-5036.
Granoff et al., 1998, "Induction of Immunologic Refractoriness in Adults by Meningococcal C Polysaccharide Vaccination", *J. Infect. Dis.* 178(3): 870-4.
Hankins, 1982, Clinical and Serological Evaluation of a Meningococcal Polysaccharide Vaccine Groups A,C,Y, and W135 (41306), Proc. Soc. Biol. Med. 169: 54-57.
Hong et al., 1981, "Inhibitory Effect of K-76 Monocarboxylic Acid, an Anticomplementary Agent, on the C3b Inactivator System" *J Immunol.* 127:104-108.
Harris SL, et al, "Age-related disparity in functional activities of human group C serum anticapsular antibodies elicited by meningococcal polysaccharide vaccine," Infect Immun 2003;71:275-86.
Holst et al., Serum bactericidal activity correlates with the vaccine efficacy of outer membrane vesicle vaccines against *Neisseria meningitidis* serogroup B disease. Vaccine 2003, 21:734-737.
MacDonald et al., 1998, "Induction of Immunologic Memory by Conjugated vs Plain Meningococcal C Polysaccharide Vaccine in Toddlers", *JAMA* 280:1685-1689.
MacDonald et al., 2000, "Can Meningococcal C Conjugate Vaccine Overcome Immune Hyporesponsiveness Induced by Previous Administration of Plain Polysaccharide Vaccine?" JAMA 283:1826-1827.
MacLennan et al., 2000, "Safety, Immunogenicity, and Induction of Immunologic memory by a Serogroup C Meningococcal Conjugate Vaccine in Infants" JAMA 283: 2795-2801.
Maiden et al., 1998, "Multilocus sequence typing: A portable approach to the identification of clones within populations of pathogenic microorganisms", *Proc. Natl. Acad. Sci.* USA 95:3140-3145.
Martin et al., 2000. "Candidate *Neisseria meningitidis* NspA vaccine", *J. Biotechnol.* 83:27-31.
Martin et al, 2000, "Effect of sequence variation in meningococcal PorA outer membrane protein on the effectiveness of a hexavalent PorA outer membrane vesicle vaccine", *Vaccine*, 18:2476-2481.
Moe et al. 1999,"Differences in Surface Expression of NspA among *Neisseria meningitidis* Group B Strains", *Infection and Immunity*, 67:5664-5675.
Moe et al. 1999, "Molecular Mimetics of Polysaccharide Epitopes as Vaccine Candidates for Prevention of *Neisseria* Menignitidis Serogroup B Disease", FEMS Immunology and Medical Microbiology 26, 209-226.

(56) References Cited

OTHER PUBLICATIONS

Moe et al. 2001, "Functional Activity of Anti-Neisserial Surface Protein A Monoclonal Antibodies against Strains of *Neisseria meningitidis* Serogroup B", *Infection and Immunity*, 69:3762-3771.

Milagres et al., 1994, "Immune Response of Brazilian Children to a *Neisseria meningitidis* Serogroup B Outer Membrane Protein Vaccine; Comparison with Efficacy", *Infection and Immunity*, 62: 4419-4424.

Maslanka SE, et al. "Age-dependent *Neisseria meningitidis* serogroup C class-specific antibody concentrations and bactericidal titers in sera from young children from Montana immunized with a licensed polysaccharide vaccine," Infect Immun 1998;66:2453-9.

Nicholson A, Lepow IH. "Host defense against *Neisseria meningitidis* requires a complement-dependent bactericidal activity," Science 1979;205:298-9.

Pollard AJ, et al, "Development of natural immunity to *Neisseria meningitides*," Vaccine 2001;19:1327-46.

Pizza et al. 2000 "Identification of Vaccine Candidates Against Serogroup B Meningococcus by Whole-Genome Sequencing", *Science* 287:1816-1820.

Rouppe Van Der Voort et al., 2000, "Immunogenicity studies with a genetically engineered hexavalent PorA and a wild-type meningococcal group B outer membrane vesicle vaccine in infant cynomolgus monkeys", *Vaccine*, 18:1334-1343.

Rouppe Van Der Voort et al., 1997, Human B- and T-cell responses after immunization with a hexavalent PorA meningococcal outer membrane vesicle vaccine. Infect Immun. Dec;65(12):5184-90.

Sacchi et al., 1998, "Correlation between Serological and Sequencing Analyses of the PorB Outer Membrane Protein in the *Neisseria meningitidis* Serotyping System", *Clin. Diag. Lab. Immunol.* 5:348-354.

Sacchi et al., 2000, "Diversity and Prevalence of PorA Types in *Neisseria meningitidis* Serogroup B in the United States", *Journal of Infectious Diseases*, 182:1169-1176.

Saukkonen et al. 1988, "Monoclonal Antibodies to the Rough Lipopolysaccharide of *Neisseria meningitidis* Protect Infant Rats From Meningococcal Infection" *Journal of Infectious Diseases*, 158: 209-212.

Shag-Qing, et al., 1981, "Three new serogroups of *Neisseria meningitidis*", J. Biol. Stand. 9: 307-315.

Slaterus, K. W., 1961, Ant. V. Leeuwenhoek, "Types of Meningococcal Isolated from Carriers and Patients ina Non-Epidemic Period in the Netherlands", *J. Microbiol. Serol.* 29: 265-271.

Stephens et al. 1991, "Insertion of Tn916 in *Neisseria meningitidis* Resulting in Loss of Group B Capsular Polysaccharide", *Infection and Immunity*, 59: 4097-4107.

Tappero et al., 1999, "Immunogenicity of 2 Serogroup B Outer-Membrane Protein Meningococcal Vaccines", *JAMA* 281:1520-1572.

Wyle et al., 1972, "Immunologic Response of Man to Group B Meningococcal Polysaccharide Vaccines", *J Infect. Dis.* 126: 514-522.

Zollinger, et al., 1979, "Complex of Meningococcal Group B Polysaccharide and Type 2 Outer Membrane Protein Immunogenic in Man", *J Clin. Invest.* 63: 836-848.

Naess, et al. 1998, "Human T-Cell Response after Vaccination with the Norwegian Group B Meningococcal Outer Membrane Vesicle Vaccine" *Infection and Immunity*, vol. 66(3): 959-965.

Haneberg et al. 1998, "Intranasal Administration of a Meningococcal Outer Membrane Vesicle Vaccine Induces Persistant Local Mucosal Antibodies and Serum Antibodies with Strong Bactericidal Activity in Humans", *Infection and Immunity*, vol. 66(4): 1334-1341.

Wedege et al. 1998, "Immune Response against Major Outer Membrane Antigens of *Neisseria meningitidis* in Vaccines and Controls Contracted Meningococcal Disease during the Norwegian Serogroup B Protection Trail", *Infection and Immunity*, vol. 66(7): 3223-3231.

Lehmann et al. 1999, "Human Opsonins Induced during Meningococcal Disease Recognize Outer Membrane Proteins PorA and PorB", *Infection and Immunity*, vol. 67(5):2552-2560.

Rosenqvist et al. "Human Antibody Responses to Meningococcal Outer Membrane Antigens after three Doses of the Norwegian Group B Meningococcal Vaccine", *Infection and Immunity*, vol. 63(12): 46-42-4652, 1995.

World Health Organization. Requirements for meningococcal polysaccharide vaccine (requirements for biological substances No. 23). WHO Tech Rep Ser 1976;594:72-73.

50 Fed. Reg. 162, Guidelines for Production of Meningococal Polysaccharide Vaccines Docket No. 84D-0263, Notice of Availability Published Aug. 21, 1985.

\* cited by examiner

Summary of meningococcal outer membrane vesicle vaccine efficacy trials*

| Years of the Study | Vaccine Strain | Location (population vaccinated) | Age (years) | Estimated Efficacy (%) |
|---|---|---|---|---|
| 1987-89 | B:4:P1.15 C PS/alum | Cuba (100,000 school children) | 11 to 16 | 83 |
| 1989-90 | B:4:P1.15 C PSb/alum | Sao Paolo, Brazil (300,000 children) | 2 to 4 <br> 4.1 to 7 | 47 <br> 74 |
| 1990-91 | B:4:P1.15 C PS/alum | Rio de Janeiro, Brazil (2.4 million children) | 3/12 to 7 <br> 4. to 7 | 58 <br> 71 |
| 1988-90 | B:4:P1.3 C PS/alum | Iquique, Chile (40,000 children) | 1 to 3.9 <br> 4 to 21 | -23 <br> 70 |
| 1989-91 | B:15:P1.7,16 alum | Norway (171,800 school children) | 14. to 16 | 57 |

*Adapted from Frasch (1995), in MENINGOCOCCAL DISEASE, K. Cartwright (ed.), Wiley, New York, NY, p. 266). In Norway, two doses of vaccine were given separated by 6 weeks. Efficacy was 87% in the first year and then declined during the subsequent 18 months follow-up, so that overall efficacy was 57%. C PS=Serogroup C polysaccharide vaccine that is mixed with the vesicles. Alum preparations were $Al(OH)_3$

FIG. 1

Bacterial cell surface binding of antisera determined by indirect fluorescence flow cytometry

| Strain (serosubtype) | PorA heterologous to CHORI vaccine strains [+++] | Surface reactivity by indirect fluorescence flow cytometry (1/titer)[+] | | |
|---|---|---|---|---|
| | | Anti-CHORI[++] | Anti-Norway[++] | Anti-NspA[++] |
| 1000 (5) | - | >200 | >200 | 20 |
| 2996 (5,2) | - | 2000 | <20 | 20 |
| 8047 (5,2) | - | >200 | <20 | >20 |
| BZ198 (4) | - | 2000 | 200 | >20 |
| CU385 (19,15) | + | >200 | <20 | >20 |
| IH5341 (7,16) | + | >200 | >200 | <20 |
| M136 (P-) | ± | <20 | <20 | <20 |
| M986 (5,2) | - | 2000 | <20 | <20 |
| MC58 (7,16) | + | 200 | >200 | <20 |
| NG3/88 (1) | + | 200 | 200 | >20 |
| NMB (.5,2) | - | 2000 | ND | >20 |
| S3446 (23,14) | + | 200 | <20 | <20 |

[+] Titer is defined as the dilution required to give 50% of fluorescence (FL1-Height) of 10 or greater over background fluorescence of cells in the presence of control sera.

[++] Anti-CHORI antisera prepared in mice by sequential immunization with MV from strain RM1090 (C:2a;P1.5,2), then with MV from strain BZ198 (B:NT:P1.4) followed by OMV from strain Z1092 (A:4,21;P1.10) (see text). AntiNorway refers to antiserum from guinea pigs given two injections of OMV vaccine prepared from strain H44/76 (B:15:P1.7,16) by the National Institute of Public Health ("MenB-Folkehelsa"), Oslo, Norway. Anti-NspA refers to antisera prepared in CD1 mice given three injections of recombinant NspA as described by Moe et al. (1999 Infect. Immun. 67: 5664).

[+++] Serosubtype (PorA) differs from those of the three strains used to prepare the vaccine. (see FIG. 21 and 22).

FIG. 4

Reactivity of CHORI antisera against N. meningitidis serogroup A and C strains

| Strain (serogroup:serosubtype) | Bactericidal Activity (1/titer)* | | Surface binding by indirect fluorescence flow cytometry (1/titer)+ | |
|---|---|---|---|---|
| | Negative control sera | Anti-CHORI | Negative control sera | Anti-CHORI |
| 60E (C:P1.7,1) | <10 | >250 | <20 | ~2000 |
| Z1073 (A:P1.3,6) | <10 | >250 | ND | >>100 |

*Dilution of serum yielding 50% decrease in colony forming units (CFU) per ml after 60 minutes incubation of bacteria in the presence of human complement as compared to CFU/ml at time zero of controls (see FIG. 6 below).

+See footnotes to FIG. 4 and text

FIG. 5

Results of a bactericidal assay testing anti-CHORI antigen, anti-rNspA, and anti-Norwegian vaccine antisera against meningococcal B strain 2996

| Complement | Animal source of sera or mAb | Antibody/Antisera+ | Final Concentration/Dilution | CFU/20 µl 0' | CFU/20 µl 60' | % Survival |
|---|---|---|---|---|---|---|
| None | - | None | 0 | 189 | 250 | 132 |
| None | - | None | 0 | 171 | 250 | 146 |
| Active | - | None | 0 | 175 | 250 | 143 |
| Inactive | - | None | 0 | 180 | 250 | 139 |
| Active | - | Complement | 1:5 | 190 | 250 | 132 |
| Active | Mouse | Anti-capsular mAb | 200µg/ml | | 1 | 1 |
| Active | Mouse | Anti-capsular mAb | 100µg/ml | | 43 | 24 |
| Active | Mouse | Anti-capsular mAb | 50µg/ml | | 225 | 124 |
| Inactive | Mouse | Anti-capsular mAb | 200µg/ml | | 230 | 127 |
| Active | Mouse | Anti-rNspA | 1:10 | | 250 | 138 |
| Active | Mouse | Anti-rNspA | 1:50 | | 250 | 138 |
| Active | Mouse | Anti-rNspA | 1:250 | | 250 | 138 |
| Active | Mouse | Anti-CHORI antigen | 1:10 | | 0 | 0 |
| Active | Mouse | Anti-CHORI antigen | 1:50 | | 2 | 1 |
| Active | Mouse | Anti-CHORI antigen | 1:250 | | 55 | 30 |
| Active | Mouse | Anti-E. coli control | 1:10 | | >250 | 138 |
| Active | Guinea pig | Anti-Norwegian vaccine | 1:5 | | 220 | 122 |
| Active | Guinea pig | Anti-Norwegian vaccine | 1:25 | | 245 | 135 |
| Active | Guinea pig | Anti-Norwegian vaccine | 1:125 | | 250 | 138 |
| Active | Guinea pig | Anti-alum control | 1:5 | | 250 | 138 |

+See footnotes to FIG. 4 and text

FIG. 6

Complement-mediated bactericidal activity of antisera and antibodies.

| Strain (serosubtype) | PorA heterologous to CHORI vaccine strains | Bactericidal activity (1/titer) [+] | | |
|---|---|---|---|---|
| | | Anti-CHORI | Anti-Norway | Anti-NspA |
| 1000 (5) | - | 130 | >125 | <10 |
| 2996 (5,2) | - | >250 | <5 | <10 |
| 8047 (5,2) | - | >250 | <5 | <10 |
| BZ198 (4) | - | >250 | I[++] | 110 |
| CU385 (19,15) | + | >250 | <25 | <10 |
| IH5341 (7,16) | + | >250 | I[++] | <10 |
| M136 (P-) | + | <10 | <5 | <10 |
| M986 (5,2) | - | >250 | <5 | <10 |
| MC58 (7,16) | + | >250 | >125 | <10 |
| NG3/88 (1) | + | 13 | 9 | <10 |
| NMB (5,2) | - | >100 | <5 | 16 |
| S3446 (23,14) | + | 10 | <5 | <10 |

+See footnotes to FIGS. 4 and 5 and text. Titer > refers to highest dilution tested; titer < refers to lowest dilution tested
++I, indeterminate due to the presence of bactericidal activity in the negative control antisera against this strain.

FIG. 7

Complement-mediated bactericidal activity of antisera from mice immunized with the indicated vaccines.

| Strain (serosubtype) | PorA heterologous to CHORI vaccine strains[+++] | Bactericidal activity (1/titer)[+++] | | | |
|---|---|---|---|---|---|
| | | CHORI CFA[+] (N=7) | CHORI/ Al$_2$(OPO$_4$)$_3$[+] (N=7) | CHORI MIX/ Al$_2$(OPO$_4$)$_3$[+] (N=10) | E. COLI MV/ Al$_2$(OPO$_4$)$_3$[+] (N=10) |
| 1000 (5) | - | 20 | 128 | 6 | <4 |
| 8047 (5,2) | - | 125 | 300 | 125 | <25 |
| BZ198 (4) | - | 650 | 220 | 1000 | <4 |
| BZ198 NspA (4) | - | 317 | 131 | 235 | <4 |
| BZ83 (10) | - | 275 | 109 | 205 | <25 |
| CU385 (19,15)[++] | + | >128 | 128 | <4 | <5 |
| H44/76 (7,16) | + | >128 | >128 | 21 | 6 |
| M136 (P-) | + | 100 | <4 | 5 | <4 |
| M986 (5,2) | - | 193 | 101 | 133 | <4 |
| MC58 (7,16)[++] | + | 47 | 8 | 7 | <4 |
| NG3/88 (7,1) | + | <4 | 4 | <4 | <4 |
| NGP165 (5,2) | - | 82 | 120 | 90 | <4 |
| NMB (5,2) | - | 183 | 441 | 141 | <4 |
| S3032 (12,16) | + | 125 | 400 | 230 | <25 |
| S3446 (22,14) | + | 18 | <4 | <4 | <4 |

[+]CHORI/CFA, sequential Immunization with a 5 µg dose of strain RM1090 (C:2a;P1.5,2) MV with CFA, strain BZ198 (B:NT:P1.4) MV with IFA, and strain Z1092 OMV (A:4,21:P1.10) without adjuvant; CHORI/Al$_2$(OPO$_4$)$_3$ same as CHORI/CFA except using aluminum phosphate as an adjuvant; CHORI MIX/Al$_2$(OPO$_4$)$_3$, same as CHORI/ Al$_2$(OPO$_4$)$_3$ except each 5 µg dose contained an equal mixture of the three MV/OMV preparations; E. COLI MV/Al2(OPO$_4$)$_3$ MV prepared from E. coli strain BL21(DE3).
[++]w/glu, cell culture grown in the presence of 0.3% glucose. [+++]See footnotes and text of FIG. 4.

FIG. 8

Bactericidal activity of antisera from guinea pigs immunized with the indicated vaccines[+].

| Strain (serosubtype)[++] | PorA heterologous to CHORI vaccine strains[+++] | Bactericidal activity (1/titer)[+++] | | |
|---|---|---|---|---|
| | | CHORI/Al$_2$(OPO$_4$)$_3$ (N=8) | CHORI/Al(OH)$_3$ (N=3) | E. COLI MV/Al$_2$(OPO$_4$)$_3$ (N=6) |
| M136 (P-) | + | <4 | <4 | <4 |
| S3446 (22,14) | + | 6 | 4 | <4 |
| CU385 (19,15) | + | 12 | 5 | <4 |
| 1000 (5) | - | 64 | 16 | <4 |
| H44/76 (7,16) | + | 64 | 16 | <4 |
| BZ83 (10) | - | 24 | 12 | <4 |
| 8047 (5,2) | - | >128 | 100 | <4 |
| BZ198 (4) | - | 28 | 6 | <4 |
| BZ198ΔNspA (4) | - | 19 | 5 | <4 |
| NG3/88 (7,1)++ | + | 9 | 5 | <4 |

[+]CHORI/Al$_2$(OPO$_4$)$_3$, sequential immunization with a 5 microgram dose of strain RM1090 (C:2a,P1.5,2) MV, strain BZ198 (B:NT:P1.4) MV, and strain Z1092 OMV (A:4,21:P1.10) aluminum phosphate as an adjuvant; CHORI/Al(OH)$_3$, same as CHORI/Al$_2$(OPO$_4$)$_3$ except using aluminum hydroxide as an adjuvant; E. COLI MV/Al$_2$(OPO$_4$)$_3$, MV prepared from E. coli strain BL21(DE3).
[++]All strains were grown in the presence of 0.3% glucose except for strains M136 and NG3/88.
[+++]See footnotes and text of FIG. 4.

FIG. 9

Passive protection in infant rats against meningococcal B strain 8047 bacteremia by antisera and antibodies.+

| Treatment++ | Dose/rat or Serum Dilution (100 microliters) | Blood Culture Obtained at 18 hrs | |
|---|---|---|---|
| | | No. Positive/total no. | Geo. Mean, $10^3$ CFU/ml |
| Anti-Capsular mAb | 10 micrograms | 0/5 | <1 |
| PBS control | - | 5/5 | >200 |
| Anti-E. coli control | 1:20 | 5/5 | >200 |
| Anti-CHORI | 1:20 | 0/5 | <1 |
| Anti-Norway | 1:20 | 5/5 | 83 |
| Alum control | 1:20 | 5/5 | 178 |

+Animals were pretreated at time 0 with control or test antibodies and challenged 2 hours later with 5 x $10^3$ colony forming units of log phase N.meningitidis strain 8047 given IP.
++See footnotes to FIG. 4 and text.

FIG. 10

FIG. 11. Passive protection in infant rats against meningococcal B strain 8047 bacteremia by guinea pig antisera.

| Treatment[+] | Dose/rat or Serum Dilution (100 microliters) | Blood Culture Obtained at 18 hrs | |
|---|---|---|---|
| | | No. Positive/total no. | Geo. Mean, $10^3$ CFU/ml |
| Pre-immnization | 1:10 | 6/6 | 21.9 |
| Anti-CHORI/ $Al_2(OPO_4)_3$ | 1:10 | 0/6 | <0.001 |
| Anti-CHORI/ $Al_2(OPO_4)_3$ | 1:100 | 4/6 | 1.3 |
| Anti-CHORI/ $Al_2(OPO_4)_3$ | 1:1000 | 6/6 | 193 |
| Anti-CHORI/Al(OH)$_3$ | 1:10 | 0/6 | <0.001 |
| Anti-CHORI/Al(OH)$_3$ | 1:100 | 6/6 | 47.4 |
| Anti-CHORI/Al(OH)$_3$ | 1:1000 | 6/6 | 32.0 |
| Anti-E. coli MV | 1:10 | 6/6 | 110 |
| Mouse anti-capsular mAb (SEAM 3) | 20 µg | 3/3 | 1.4 |

[+]See footnotes to FIGS. 9 and 10 and text.

Bacterial surface accessible proteins precipitated by pooled antisera from mice sequentially immunized with MenC strain RM1090 MV, MenB strain BZ198 MV, and MenA strain Z1092 OMV.

| Strain/Sample | Serotype:subtype[+] | Precipitated Proteins (by apparent mass in kDa) | | |
|---|---|---|---|---|
| | | 37-41 | 31-33 | <30 |
| RM1090MV | 2a:P1.5,2:L3,7 | 40.7, 39.6 | 32 | |
| BZ198 MV | NT:NST | 37.1, 35.1 | 32,30 | |
| Z1092 OMV | 4,21:P1.10 | 40.7, 39.1, 38.6, 37.6 | 33.1, 32.5, 31.5 | |
| BZ198 | NT:NST | | 32.5 | 14.5 |
| CU385 | 4,7:P1.19,15 | | 32.4 | |
| MC58 | 15:P1.7,16 | | 32.9 | |
| NG3/88 | 8:P1.1 | | 32.9 | 25.7 |
| NMB | 2b:P1.5,2 | 40.7, 39.6 | 33 | 14.5 |
| S3446 | 19,14:P1.23,14 | | 32.9 | 25.7 |

[+]See text and footnotes of Tables 21 and 22 (below)

FIG. 14

Bacterial surface accessible proteins precipitated by pooled antisera from mice sequentially immunized with MenC strain RM1090 MV, MenB strain BZ198 MV, and MenA strain Z1092 OMV.

| Strain | Serotype:subtype + | Precipitated Proteins (by apparent mass in kDa) | | | | | | | |
|---|---|---|---|---|---|---|---|---|---|
| | | >45 | | 36-45 | | 25-35 | | <25 | |
| | | Expt 1 | Expt 2 | Expt 1 | Expt 2 | Expt 1 | Expt 2 | Expt 1 | Expt 2 |
| BZ198 | NT:NST | 80 | | 36,39,43 | 37,40 | 28,30 | 28 | 14.5 | 12 |
| CU385 | 4,7:P1.19,15 | 80 | | 38,42 | 42 | 30,34 | ND | 10 | 11 |
| 1000 | NT:P1.5 | | ND | 41,45 | ND | 26 | ND | | ND |

FIG. 14A

+See text and footnotes of FIGS. 21 and 22 (below). Expts 1 and 2 refer to experiments performed with immune serum pools from different groups of mice immunized with different CHORI vaccine preparations. ND= not done (strain 1000 tested with immune serum from one group of immunized mice).

Proteins reactive with anti-CHORI antigen antisera by Western blot of MV and OMV preparations

| Mouse anti-CHORI/CFA antisera[+] | | | Mouse anti-CHORI Al$_2$(OPO$_3$)$_2$ antisera[+] | | Guinea pig anti-CHORI/Al$_2$(OPO$_3$)$_2$ antisera[++] | | |
|---|---|---|---|---|---|---|---|
| RM1090 MV | BZ198 MV | Z1092 OMV | BZ198 MV | Z1092 OMV | RM1090 MV | BZ198 MV | Z1092 OMV |
|  | 119 |  |  |  |  |  |  |
|  |  |  |  | 116 |  |  |  |
| 108 |  |  |  | 107 |  |  |  |
| 101 |  | 101 | 101 |  |  |  |  |
|  | 96 | 97 | 95 | 99 |  |  |  |
|  | 93 | 93 | 91 | 94 |  |  | 92 |
|  |  | 88 |  | 92 |  |  |  |
|  |  | 81 |  | 78 |  |  |  |
|  |  | 76 |  |  |  |  | 76 |
|  |  | 69 |  |  |  |  | 68 |
| 67 | 67 |  |  | 67 | 66 |  | 64 |
|  |  |  |  | 64 | 62 |  |  |
|  |  |  |  |  |  |  | 59 |
| 53* | 56* | 57* | 56 | 51 | 53 | 55 |  |
|  | 50 | 50 |  |  |  |  |  |
| 46* | 47* | 47* | 47 | 46 | 47 | 46 | 46 |
|  | 36 | 38 |  |  |  | 34 |  |
| 33* | 33* | 35* | 33 | 33 | 32 | 33 | 33 |
|  | 27 |  |  |  | 24 |  |  |
| 20* | 20* | 21* | 20 | 21 |  | 20 |  |
|  |  | 19 |  | 19 | 19 |  | 19 |
| 18* | 18* | 18* | 18 | 18 |  |  |  |

[+] See footnote and text of FIG. 8.
[++] See footnote and text of FIG. 9.
*Indicates proteins most reactive with CHORI/CFA antisera and common to at least two of the three vaccine preparations.

FIG. 16

FIG. 17. Reactivity of anti-CHORI antisera with LOS by ELISA

| Antisera[+] | RM1090 LOS (1/titer)[++] | | BZ198 LOS (1/titer)[++] | | Z1092 LOS (1/titer)[++] | |
|---|---|---|---|---|---|---|
| | Unabsorbed | Absorbed[++++] | Unabsorbed | Absorbed[++++] | Unabsorbed | Absorbed[++++] |
| Mouse anti-CHORI | <100 | <100 | 900 | <100 | 150 | <100 |
| Mouse anti-CHORI mix | 900 | 100 | 200 | <100 | 600 | 100 |
| Guinea pig anti-CHORI | <100 | <100 | 350 | 100 | <100 | <100 |
| Guinea pig anti-CHORI mix[+++] | <100 | <100 | 300 | 100 | <100 | <100 |

+ See footnotes and text of FIG. 8 and 9.

++ Titer is defined as the dilution of serum giving an OD 405 nm of 0.5 after 1 hr incubation with substrate.

+++ Same as used to prepare mouse anti-CHORI antisera mix (see FIG. 8) except that total dose of 25 micrograms protein was given rather than 5 micrograms.

++++ After incubation with LOS-BSA coupled to Sepharose (see text).

Bactericidal activity of anti-CHORI antisera before and after absorption of anti-LOS antibodies.

| Serum[+++] | Strain BZ198 (1/titer)[+] | | Strain S3032 (1/titer)[+] | |
|---|---|---|---|---|
| | Unabsorbed | Absorbed[++] | Unabsorbed | Absorbed[++] |
| Mouse anti-CHORI | 49 | 28 | 259 | 247 |
| Mouse anti-CHORI MIX | 350 | 111 | 234 | 102 |
| Guinea pig anti-CHORI | 125 | 93 | 13 | 5 |
| Guinea pig mix | 77 | 31 | <5 | 14 |

[+]See footnote and text to FIG. 5.
[++]After incubation with LOS-BSA coupled to Sepharose (see text).
[+++]See footnote and text to FIG. 17

FIG. 18

Reactivity of mAbs produced by immunization with CHORI vaccine with bacterial strains, LOS, and rNspA by ELISA.

| Strain+ | [mAb] (ng/ml) giving OD 405 nm = 0.5 after 1 hr incubation with substrate | | | | |
|---|---|---|---|---|---|
| | 1D9 (IgG2a) | 4B11 (IgM) | 9B8 (IgG3) | 14C7 (IgG3) | Anti-NspA mAb ALA+++ (IgG2a) |
| Nm 1000 | 500 | >720++ | >3970 | 7380+ | 1000 |
| Nm 4335 | 500 | >720 | 13 | 30 | 30 |
| Nm 8047 | 200 | 2.4 | >3970 | 10 | 20 |
| Nm 8047 ΔNspA | 600 | >720 | >3970 | >7380 | >5400 |
| Nm BZ198 | 600 | >720 | 16 | 2 | 20 |
| Nm BZ198 ΔNspA | 600 | >720 | 16 | >7380 | >5400 |
| Nm BZ83 | 600 | >720 | >3970 | 273 | 80 |
| Nm CU385 | 600 | >720++ | >3970 | >7380++ | 180 |
| Nm M136 | 600 | >720 | >3970 | 36 | 400 |
| Nm M3966 | 1000 | >720 | >3970 | 0.5 | 50 |
| Nm M986 | 800 | >720 | >3970 | 5 | 400 |
| Nm NG3/88 | 600 | 0.8 | >3970 | 1 | 70 |
| Nm NGE31 | 500 | >720 | >3970 | 5 | 100 |
| Nm NGF26 | 600 | 2.4 | >3970 | 0.4 | 40 |
| Nm S3446 | 500 | >720 | >3970 | 0.2 | 40 |
| Hi Minn A | >8300 | >720 | >3970 | >7380 | ND |
| Hi Eagan | >8300 | >720 | >3970 | >7380 | ND |
| Nm RM1090 LOS | >8300 | >720 | >3970 | >7380 | ND |
| Nm BZ198 LOS | >8300 | >720 | >3970 | >7380 | ND |
| Nm Z1092 LOS | >8300 | >720 | >3970 | >7380 | ND |
| rNspA MV | >8300 | >720 | >3970 | 28 | 6 |

+Nm, *Neisseria meningitidis*; Hi, *Haemophilus influenzae*

++Although negative by ELISA, 14C7 is bactericidal for these strains (see FIG. 20).

+++See Moe et al. Infect Immun. 2001 69:3762)

FIG. 19

Bactericidal activity of mAbs produced by immunization with CHORI vaccine.

| Strain (serosubtype) | PorA heterologous to CHORI vaccine strains[+] | mAb tested for bactericidal activity[++] | | | | | |
|---|---|---|---|---|---|---|---|
| | | 1D9 | 4B11 | 9B8 | 14C7 | AL12[+++] | |
| 1000 | - | - | + | - | + | + | |
| BZ198 | - | - | static | + | + | + | |
| BZ198ΔN spA | - | - | - | + | - | - | |
| CU385 | + | - | + | - | + | - | |
| M986 | - | - | - | - | + | - | |
| NG3/88 | + | - | static | - | static | - | |

[+] See text and footnotes of FIG. 4.
[++] + refers to bactericidal when tested at less than or equal to 100 micrograms/ml; static refers to a percent survival of CFU/ml at 60 min is greater then 50% but less than 100% (see FIG. 6)
[+++] Moe et al. Infect Immun. 2001 69:3762

FIG. 20

Meningococcal serotype and serosubtype defining monoclonal antibodies available from RIVM*

| Serotyping reagents | | | Serosubtyping reagents | | |
|---|---|---|---|---|---|
| Monoclonal | Type | Ig | Monoclonal | Type | Ig |
| MN3C6B | 1 | G2b | MN14C2.3 | P1.1 | G2a |
| MN2D3F | 2A | G2a | MN16C13F4 | P1.2 | G2a |
| MN2C3B | 2B | G2a | MN20B9.34 | P1.4 | G2a |
| MN14G21 | 4D | G2a | MN22A9.19 | P1.1.5 | G2a |
| MN5C8C | 14 | G2a | MN19D6.13 | P1.6 | G3 |
| MN15A14H6 | 15 | G2a | MN14C11.6 | P1.7 | G2a |
| | | | MN5A10F | P1.9 | G2a |
| | | | MN5A10F | P1.9 | G2a |
| | | | MN20F4.17 | P1.10 | G2b |
| | | | MN20A7.10 | P1.12 | G3 |
| | | | MN24H10.75 | P1.13 | G2a |
| | | | MN21G3.17 | P1.14 | G3 |
| | | | MN3C5C | P1.15 | G3 |
| | | | MN5C11G | P1.16 | G2b |

*Rijksinstituut Voor Volksgezondheid en Mileu (RIVM), P.O. Box 457, 3720 AL Bilthoven, The Netherlands (reference *FEMS Microbiology Letters* 48 (1987) 367-371).

FIG. 21

FIG. 22. Serogroup, serotype, and serosubtype defining monoclonal antibodies available from NIBSC*

| Serogroup | Cat. No. | Serotype | Cat. No. | Serosubtype | Cat. No. |
|---|---|---|---|---|---|
| A | 95/674 | P2.2a | 95/682 | P1.1 | 95/694 |
| B | 95/750 | P2.2b | 95/684 | P1.10 | 95/710 |
| C | 95/678 | P3.1 | 95/680 | P1.12 | 95/712 |
| | | P3.14 | 95/688 | P1.13 | 95/714 |
| | | P3.15 | 95/690 | P1.14 | 95/716 |
| | | P3.21 | 95/692 | P1.15 | 95/718 |
| | | P3.4 | 95/686 | P1.16 | 95/720 |
| | | | | P1.2 | 95/696 |
| | | | | P1.3 | 95/698 |
| | | | | P1.4 | 95/700 |
| | | | | P1.5 | 95/702 |
| | | | | P1.6 | 95/704 |
| | | | | P1.7 | 95/706 |
| | | | | P1.9 | 95/708 |

*National Institute for Biological Standards and Control (NIBSC), Division of Bacteriology, Blanche Lane, South Mimms, Potters Bar, Herts, EN6 3QG, United Kingdom.

VACCINES FOR BROAD SPECTRUM PROTECTION AGAINST *NEISSERIA MENINGITIDIS*

CROSS-REFERENCE TO RELATED APPLICATIONS

This application claims the benefit of earlier-filed U.S. provisional application Ser. No. 60/221,495, filed Jul. 27, 2000, which application is incorporated herein by reference in its entirety.

STATEMENT REGARDING FEDERALLY SPONSORED RESEARCH

This invention was made with government support under grants no. AI46464 and AI45642 awarded by the National Institute of Allergy and Infectious Diseases, and the National Institute of Health. The government may have certain rights in this invention.

FIELD OF THE INVENTION

This invention relates to broad-spectrum vaccines for the prevention of diseases caused by *Neisseria meningitidis*, especially serogroup B.

BACKGROUND OF THE INVENTION

*Neisseria meningitidis* is a Gram-negative bacteria which colonizes the human upper respiratory tract and is responsible for worldwide sporadic and cyclical epidemic outbreaks of, most notably, meningitis and sepsis. The attack and morbidity rates are highest in children under 2 years of age.

Like other Gram negative bacteria, *Neisseria meningitidis* typically possess a cytoplasmic membrane, a peptidoglycan layer, an outer membrane which together with the capsular polysaccharide constitute the bacterial wall, and pili which project into the outside environment. These surface structures mediate infection and interact with the host immune system. For example, a first step in infection with *Neisseria* is adherence to target cells, which is thought to be mediated by the pili and, possibly, other adhesins such as Opc. Protein, phospholipid and polysaccharide components of the outer membrane have been reported to elicit an immune response.

*Neisseria meningitidis* spp. can be divided into serologic groups, types and subtypes on the basis of reactions with polyclonal (Frasch, C. E. and Chapman, 1973, *J. Infect. Dis.* 127: 149-154) or monoclonal antibodies (Hussein, A., MONOCLONAL ANTIBODIES AND N. MENINGITIDIS. Proefschrift. Utrecht, Nederland, 1988) that interact with different surface antigens. Serogrouping is based on immunologically detectable variations in the capsular polysaccharide. About 12 serogroups are known: A, B, C, X, Y, Z, 29-E, W-135, H, I, K and L (Ashton, F. E. et al., 1938, *J. Clin. Microbiol.* 17: 722-727; Branham, S. E., 1956, *Can. J Microbiol.* 2: 175-188; Evans, A. C., 1920, *Lab. Bull.* 1245: 43-87; Shao-Qing, et al., 1972, *J. Biol. Stand.* 9: 307-315; Slaterus, K. W., 1961, Ant. v. Leeuwenhoek, *J. Microbiol. Serol.* 29: 265-271). Currently, serogroup B (MenB) is responsible for about half to 80% of reported invasive *Neisseria meningitidis* diseases.

Serotyping is based on monoclonal antibody defined antigenic differences in an outer membrane protein called Porin B (PorB). Antibodies defining about 21 serotypes are currently known (Sacchi et al., 1998, *Clin. Diag. Lab. Immunol.* 5:348). Serosubtyping is based on antibody defined antigenic variations on an outer membrane protein called Porin A (PorA). Antibodies defining about 18 serosubtypes are currently known. Serosubtyping is especially important in *Neisseria meningitidis* strains where immunity may be serosubtype specific. Most variability between PorA proteins occurs in two (loops I and IV) of eight putative, surface exposed loops. The variable loops I and IV have been designated VR1 and VR2, respectively. Since more PorA VR1 and VR2 sequence variants exist that have not been defined by specific antibodies, an alternative nomenclature based on VR typing of amino acid sequence deduced from DNA sequencing has been proposed (Sacchi et al., 2000, *J. Infect. Dis.* 182:1169; see also the Multi Locus Sequence Typing web site). Lipopolysaccharides can also be used as typing antigens, giving rise to so-called immunotypes: L1, L2, etc.

*Neisseria meningitidis* also may be divided into clonal groups or subgroups, using various techniques that directly or indirectly characterize the bacterial genome. These techniques include multilocus enzyme electrophoresis (MLEE), based on electrophoretic mobility variation of an enzyme, which reflects the underlying polymorphisms at a particular genetic locus. By characterizing the variants of a number of such proteins, genetic "distance" between two strains can be inferred from the proportion of mismatches. Similarly, clonality between two isolates can be inferred if the two have identical patterns of electrophoretic variants at number of loci. More recently, multilocus sequence typing (MLST) has superseded MLEE as the method of choice for characterizing the microorganisms. Using MLST, the genetic distance between two isolates, or clonality is inferred from the proportion of mismatches in the DNA sequences of 11 housekeeping genes in *Neisseria meningitidis* strains (Maiden et al., 1998, *Proc. Natl. Acad. Sci. USA* 95:3140).

Given the prevalence and economic importance of invasive *Neisseria meningitidis* infections, it is not surprising that many attempts have been made to develop treatments. Although these infections can be treated with antibiotics, about 10 to 20% of treated patients die, and many survivors are left with permanent neurologic sequelae, such as amputation, neurosensory hearing loss, and paralysis. Also, microorganisms can develop antibiotic resistance. Thus, prevention with vaccines is a preferable mode to contain the spread of infection.

Because the polysaccharide capsule is one of the outermost structures of pathogenic *Neisseria meningitidis*, it has been a primary focus of attempts to develop vaccines. Different preparations of capsular polysaccharides have been used to control the outbreaks and epidemics of the serogroups A, C, Y and W-135, as mono-, di-, tri- or tetravalent vaccines (Gold et al., 1969-1970, *Bull. WHO* 45: 272-282; Gotschlich et al., 1969, *J. Exp. Meal* 129: 134-136; Hankins, 1982, *Proc. Soc. Biol. Med.* 169: 54-57; U.S. Pat. No. 6,080,589). However, capsular polysaccharide vaccines suffer from: poor or no-response to polysaccharide C in children under 2 years of age; thermolability of polysaccharide A; difficulties regarding the induction of immunologic tolerance after vaccination or re-vaccination with polysaccharide C (Granoff et al., 1998, *J. Infect. Dis.* 160: 5028-5030; MacDonald et al., 1998, *JAMA* 280:1685-1689; MacDonald et al., 2000, *JAMA* 283: 1826-1827). To circumvent these immunologic properties, polysaccharides from serogroups A and C have been covalently coupled to protein carriers to make "conjugate" vaccines. In contrast to plain polysaccharide vaccines, these conjugate vaccines are highly immunogenic in infants, upon re-injection elicit boostable increases in serum anticapsular antibody concentrations, and prime for the ability to generate memory antibody responses to a subsequent injection of plain polysaccharide (Campagne et al. 2000, *Pediat. Infect. Dis.* J. 19:

144-150; Maclennan et al., 2000, *JAMA* 283: 2795-2801). Conjugate vaccines with similar properties have been highly effective in preventing invasive diseases caused by other encapsulated bacteria, such as *Haemophilus influenzae* type b or *Streptococcus pneumoniae*.

The capsular polysaccharide (PS) of serogroup B *Neisseria meningitidis* is a very poor immunogen in humans (Wyle et al., 1972, *J. Infect. Dis.* 126: 514-522; Zollinger, et al., 1979, *J. Clin. Invest.* 63: 836-834; Jennings et al., 1981, *J. Immunol.* 127: 104-108). Further attempts to improve the polysaccharide's immunogenicity through conjugation to protein have been unsuccessful (Jennings et al., 1981, *J. Immunol.* 127: 104-108). To enhance the immunogenicity, the meningococcal serogroup B capsule polysaccharide (MenB PS) has been chemically modified (N-propionylated group was substituted for the N-acetyl group of B polysaccharide) and coupled covalently to a protein carrier (N—Pr-MenB PS-protein) conjugate. The vaccine induces in mice high titers of IgG antibodies which are bactericidal and protective (this concept is described and claimed in U.S. Pat. No. 4,727,136, issued Feb. 23, 1988 to Jennings et al.). This vaccine also is immunogenic in sub-human primates, inducing serum antibodies that activate complement-mediated bacteriolysis (Fusco et al., 1997, *J. Infect. Dis.* 175: 364-372). In humans, such antibodies are known to confer protection against developing meningococcal disease (Goldschneider et al., 1969, *J. Exp. Med.* 129: 1307). However, a subset of the antibodies induced by this vaccine have autoantibody activity to unmodified MenB PS (i.e. N-acetyl-MenB PS), Granoff et al., 1998, *J. Immunol;* 160: 5028-5036, which raise serious safety concerns about the use of this vaccine in humans. Therefore, investigators have sought alternative approaches to develop a safe and effective vaccine for prevention of disease caused by serogroup B strains.

Other groups have focused on surface proteins as vaccines. For example, the principal protein component of the pilus, pilin, elicits an immune response; however, so many antigenic variants exist and continue to develop that vaccines against the pilus protein have not been highly effective. See, U.S. Pat. No. 5,597,572. In other examples, vaccines have focused the highly conserved *Neisserial* surface protein A (NspA) (see, e.g., PCT Publication No. WO96/29412). Although the gene is highly conserved and expressed in virtually all strains, both polyclonal and monoclonal antibodies prepared against recombinant NspA are bactericidal and/or provide protection, against only about 50% of genetically diverse strains (Moe et al. (1999 Infect. Immun. 67: 5664; Moe et al. Infect Immun. 2001 69:3762). These observations suggest that recombinant NspA alone will not provide adequate protection against a broad spectrum of *Neisserial* strains.

Still other groups have used membrane preparations to induce immunity. In general, attempts to produce a meningococcal B vaccine based on outer membrane vesicles used repeated immunizations with material prepared from a single strain or repeated immunization with a vaccine containing vesicle antigens from multiple strains. When the vaccine contained vesicle antigens from more than strain, the resulting bactericidal antibody titers of infants or children given two or three doses were low (Cartwright K et al, 1999, Vaccine; 17:2612-2619; de Kleinjn E D et al, 2000, Vaccine, 18: 1456-1466), In these studies, and in a study done in cynomolgus monkeys (Rouupe van der Voort E R, 2000, Vaccine, 18:1334-1343) there also was evidence of immune interference between the responses to the different antigen. When repeated immunization with vesicles from a single strain was used, higher antibody titers resulted but the spectrum of antibody reactivity was limited to only a few strains that tended to be serologically similar to each other (Tappero et al., 1999, *JAMA* 281:1520; and Rouupe van der Voort E R, 2000, Vaccine, 18:1334-1343). Our experiments in laboratory animal models, which are described below confirmed this latter observation. Antisera from control animals given two sequential immunizations of a outer membrane vesicle vaccine prepared at the National Institute of Public Health, Oslo, Norway, from a single *Neisseria meningitidis* serogroup B strain, H44/76 (B:15:P1.7,16; "Norwegian vaccine"), reacted by flow cytometry and were bactericidal against only serogroup B strains that were of the same serosubtype (i.e. P1.7,16) or strains having an epitope similar to the P1.16 epitope (such as P1.10-4 strains).

Humans are the only known reservoir for *Neisseria meningitidis* spp. Accordingly, *Neisserial* species have evolved a wide variety of highly effective strategies to evade the human immune system. These include expression of a polysaccharide capsule that is cross-reactive with host polysialic acid (i.e. serogroup B) and high antigenic mutability for the immunodominant noncapsular epitopes, i.e. epitopes of antigens that are present at the surface in relatively large quantities, are accessible to antibodies, and elicit a strong antibody response.

Prior efforts to develop broad spectrum vaccines have been hampered by the wide variety of highly effective strategies used by *Neisserial* species to evade the human immune system. Because of these strategies, an immune response to a given strain will often not confer effective immunity against other strains of *Neisseria*. The present invention overcomes the disadvantages of prior art approaches to vaccination and elicits protective immunity against a broad spectrum of *Neisseria meningitidis* strains, notably (but not exclusively) including strains belonging to serogroup B.

SUMMARY OF THE INVENTION

The present invention generally provides methods and vaccines for the prevention of diseases caused by *Neisseria meningitidis* bacteria, particularly serogroup B strains.

In one embodiment, the method of the invention comprises: administering to a mammal a first preparation of i) outer membrane vesicles (OMV) of a first *Neisseria meningitidis* spp., and/or ii) microvesicles (MV) released into a culture medium during culture of a first *Neisseria meningitidis* spp., said administering of OMV and/or MV being in a sufficient amount to immunologically prime and/or elicit an immune response to epitopes present in said first preparation; administering at least a second preparation of i) OMVs of a second *Neisseria meningitidis* spp., and/or ii) MVs released into a culture medium during culture of a second *Neisseria meningitidis* spp., said administering of OMV and/or MV being in a sufficient amount to immunologically prime and/or elicit an immune response to epitopes present in said second preparation; and optionally, but preferably, administering a third preparation of i) OMV of a third *Neisseria meningitidis* spp., and/or ii) MV that are released into a culture medium during culture of a third *Neisseria meningitidis* spp., said administering of OMV and/or MV being in a sufficient amount to elicit an immune response to epitopes present in said third preparation. Administration of the first, second, and (optionally) third preparation results in induction of an immune response to epitopes present in the preparations, wherein said response confers protective immunity against a disease caused by *Neisseria meningitidis* spp.

In preferred embodiments, the first, second, and third *Neisseria* strains are genetically diverse to one another, e.g., the first strain is genetically diverse to the second strain, the third strain, or both the second and third strain.

In related embodiments, administration of the preparations is serial. Serial administration of the preparations can be conducted in any order. For example, the following orders of administration are within the scope of the invention (from left to right, with the third administration being optional): OMV-OMV-OMV; OMV-OMV-MV; OMV-MV-MV; MV-MV-MV; MV-MV-OMV; MV-OMV-OMV; OMV-MV-OMV; and MV-OMV-MV. Preferably, the order of administration is MV-MV-OMV.

In other related embodiments, the preparations are administered as a mixture, where the initial administration of the mixture can be followed by one or more additional administrations of the same or different mixture to serve as boosters.

In one specific embodiment, the invention involves serially administering microvesicles (MV) that bleb naturally during growth of *Neisseria meningitidis* and are released in the culture medium (collected by separating the larger cells from the smaller blebs and then pelleting the blebs) and/or outer membrane vesicles (OMV, prepared directly from isolated outer membrane fractions). The OMVs and MVs are prepared from "genetically diverse" strains of *Neisseria meningitidis*, for example, strains that differ from one another in at least one of serotype or serosubtype, and may be diverse at multiple genetic loci, e.g., differ in both serotype and serosubtype, e.g., having different outer membrane Porin, PorA and PorB proteins. Further, the OMV and/or MV preparations can be given sequentially in at least two, and preferably at least three administrations (e.g., injections) of OMVs or MVs from genetically diverse strains; four, five, six or more administrations are also contemplated.

In another specific embodiment, the first *Neisseria meningitidis* spp. is a member of a first serosubtype; the second *Neisseria meningitidis* spp. is a member of a second serosubtype, which second subserotype are different from the subserotype of the first *Neisseria meningitidis* spp, and, where used, the third *Neisseria meningitidis* spp. is a member of a third serosubtype, which third subserotype is different from the subserotype of at least the first, and preferably both the first and the second, *Neisseria meningitidis* spp.

In still another specific embodiment, the first *Neisseria meningitidis* spp. is a member of a first serotype and of a first serosubtype; the second *Neisseria meningitidis* spp. is a member of a second serotype and of a second serosubtype, which second serotype and second subserotype are different from the serotype and subserotype of the first *Neisseria meningitidis* spp, and, where used, the third *Neisseria meningitidis* spp. is a member of a third serotype and of a third serosubtype, which third serotype and third subserotype are different from the serotype and subserotype of at least the first, and preferably both the first and the second, *Neisseria meningitidis* spp.

In one specific embodiment of the invention, a first administration is with microvesicles (MVs) prepared from a serogroup C strain (e.g. RM1090 (C:2a:P1.5,2:L3,7)). The second administration is with MVs prepared from a second strain (e.g. BZ198 (B:NT:P1.4)), and the third administration is with outer membrane vesicles (OMVs) prepared from a third strain (e.g. Z1092 (A:4,21:P1.10)). Sequential immunization with vesicles and/or microvesicles prepared from genetically diverse *Neisseria meningitidis* strains is referred to hereafter as the "CHORI vaccine" or "CHORI antigen." Immunization with a mixture of the first, second, and third preparations of the CHOR vaccine is referred to as "CHORI mix".

In other aspects, the invention features a composition comprising a first preparation selected from the group consisting of outer membrane vesicle (OMV), microvesicles (MV), or both OMV and MV from a first from a first *Neisseria meningitidis* species; a second preparation selected from the group consisting of outer membrane vesicle (OMV), microvesicles (MV), or both OMV and MV from a second *Neisseria meningitidis* species, wherein the second *Neisseria meningitidis* spp is genetically diverse to the first *Neisseria meningitidis* species; and a pharmaceutically acceptable carrier.

In related embodiments, the composition further comprises a third preparation selected from the group consisting of outer membrane vesicle (OMV), microvesicles (MV), or both OMV and MV from a third *Neisseria meningitidis* species, wherein the third *Neisseria meningitidis* species is genetically diverse to the first *Neisseria meningitidis* species. In specific embodiments, the first preparation of the composition comprises MV, the second preparation comprises MV; and the third preparation comprises OMV. Preferably, the first and second *Neisseria meningitidis* species are genetically diverse in that they differ in at least one of serotype or serosubtype, and, where included, the third and the first *Neisseria meningitidis* species are genetically diverse in that they differ in at least one of serotype or serosubtype.

In still other aspects, the invention features a composition comprising at least one isolated *Neisseria meningitidis* antigen, the isolated antigen being present in the composition in an amount effective to elicit an immune response in a mammalian host, and being characterized as a protein immunoprecipitated with anti-sera produced following vaccination with the CHORI-vaccine, and having an apparent molecular mass selected from the group consisting of about 80 kDa, about 59.5 kDa, about 40.7 kDa. about 39.6 kDa, about 33 kDa, about 27.9 kDa, and 14.5 kDa; and a pharmaceutically acceptable excipient.

In another aspect, the invention features a composition comprising at least one isolated *Neisseria meningitidis* antigen, the isolated antigen being present in the composition in an amount effective to elicit an immune response in a mammalian host, and being characterized as a protein detected by Western blot with anti-sera produced following vaccination of a mammal with the CHORI vaccine, and having an apparent molecular mass selected from the group consisting of about 53 kDa to 57 kDa; about 46-47 kDa, about 33 kDa, about 20 kDa to 21 kDa; and about 18 kDa; and a pharmaceutically acceptable excipient.

In another aspect the invention features a composition comprising at least one isolated *Neisseria meningitidis* antigen, the isolated antigen being present in the composition in an amount effective to elicit an immune response in a mammalian host, wherein the antigen is from a protein that specifically binds a monoclonal antibody selected from the group consisting of 1D9, 4B11, 9B8, and 14C7 (which antibodies are described herein and deposited with the ATCC); and a pharmaceutically acceptable excipient.

In preferred embodiments, the compositions having isolated antigens comprise at least two isolated *Neisseria meningitidis* antigens.

In related aspects, the invention features methods for eliciting broad spectrum protective immunity against a disease caused by a *Neisseria meningitidis* species, said method comprising administering to a mammal at least one of the compositions comprising isolated antigens as described above.

Preferably, the antigen compositions (e.g., OMV/MV preparations, isolated protein preparations) may be administered to mammals, especially humans, that are immunologically naïve with respect to *Neisseria meningitidis* (i.e., have not been exposed to antigens from *Neisseria meningitidis*, or have not been exposed insufficient amounts to elicit a protective immune response). A specific embodiment of the invention involves administration to human infants that are about five years old or younger, especially two years old or younger.

In some embodiments of the invention, prior to administration of antigen compositions from *Neisseria meningitidis*, the individuals may have been primed by exposure (through natural infection or administration) to a *Neisserial* species other than *Neisseria meningitidis* (or an antigen composition prepared from a *Neisserial* species).

Antisera obtained from mice immunized as described above bind to the bacterial cell surface of a group of genetically diverse *Neisseria meningitidis* serogroup B strains, as determined by flow cytometric detection of indirect immunofluorescence. In one example, sera from immunized mice were positive for eleven of 12 strains tested. These 11 included 3 meningococcal B strains with respective PorA and PorB proteins that were heterologous to those of the meningococcal strains used to prepare the immunogens used for vaccination. (By way of contrast, antisera from animals immunized with two injections of the above-described "Norwegian OMV vaccine" reacted by flow cytometry with only 5 of 11 strains. All 5 had PorA and/or PorB proteins that were the same or closely related to those in the "Norwegian" OMV vaccine.) The antisera from animals immunized with the "CHORI vaccine" also elicited complement-mediated bacteriolysis in 11 of 12 strains, a good predictor of protection against disease in humans (Goldschneider et al, 1969, J. Exp. Med. 129:1307). Antibody binding to the bacterial cell surface, or complement-mediated bacteriolysis, was not inhibited by the presence of excess soluble serogroup B polysaccharide, evidence that the protective antibodies were directed against non-capsular antigens.

Antisera from mice immunized in a second example using the CHORI vaccine were bactericidal against 14 of 14 strains tested including eight strains with serosubtypes that were heterologous from those used in the vaccine preparations. In a third example, antisera prepared from guinea pigs immunized with the CHORI vaccine were bactericidal against 9 of 10 strains tested including 5 strains with serosubtypes that were heterologous to those expressed by the vaccine strains. Antisera to the CHORI vaccine prepared in mice in the first example and in guinea pigs in the third example also were highly protective against bacteremia in the infant rats challenged with serogroup B bacteria. The immunization protocol used herein generally induces the immune system to converge on non-capsular antigens that are common to the strains from which the MVs and OMVs are obtained. The CHORI vaccine elicits antibodies against multiple cell surface epitopes, including, PorA, possibly PorB, and conserved proteins such as *Neisserial* surface protein A (NspA), the class 4 protein, (reduction modifiable protein, Rmp) and other noncapsular antigens as yet unidentified.

In general, the vaccines of the present invention that employ sequential immunization with antigenic material prepared from different strains (genetically diverse) have the potential to confer protection against the majority of *Neisseria meningitidis* serogroup B strains. This approach also has broad applicability for vaccination against *Neisseria meningitidis* strains representative of other serogroups such as A, C, Y, or W-135, and also against other members of the genus *Neisseria*.

BRIEF DESCRIPTION OF THE DRAWINGS

FIG. 1 summarizes the results of meningococcal outer membrane vesicle vaccine efficacy trials.

FIG. 2 is a photograph of a 15% SDS-PAGE gel of microvesicle (MV), deoxycholate extracted microvesicle (DOC MV), outermembrane vesicle (OMV), and deoxycholate extracted outermembrane vesicle (DOC OMV) vaccine preparations from meningococcal strains Z1092 (A:4,21: P1.10), BZ198 (B:NT:P.1.4), and RM1090 (C:2a:P1.2), respectively. Lane 1, molecular mass standards. Lane 2, Z1092 MV. Lane 3, Z1092 DOC MV. Lane 4, Z1092 OMV. Lane 5, Z1092 DOC OMV. Lane 6, BZ198 MV. Lane 7, BZ198 DOC MV. Lane 8, BZ198 OMV. Lane 9, BZ198 DOC OMV. Lane 10, RM1090 MV. Lane 11, RM1090 DOC MV. Lane 12, RM1090 OMV. Lane 13, RM1090 DOC OMV.

FIG. 3 is a series of graphs showing binding of anti-CHORI vaccine, anti-Norwegian vaccine and control antisera and mAb to live encapsulated meningococcal B strains MC58 (B:15:P1.7,16) and S3446 (B:19,14:P1.23,14), as determined by indirect fluorescence flow cytometry. All antisera were tested at dilutions of 1:20. The control mAb is an anti-capsule-specific murine mAB (Granoff et al., 1998, *J. Immunol.* 160: 5028-5036). The control antisera were pooled sera from mice immunized with proteins from the supernatant culture of *E. coli* strain BL21 or guinea pigs immunized with the adjuvant, aluminum hydroxide, alone. Note that the strain MC58 has the same serotype and serosubtype as the strain used to prepare OMV for the Norwegian vaccine. The serotype and serosubtype of strain S3446 is heterologous to the strains used to prepare both vaccines.

FIG. 4 presents data regarding the bacterial cell surface binding of antisera determined by indirect fluorescence flow cytometry FIG. 5 presents data illustrating the reactivity of CHORI antisera against *N. meningitidis* serogroup A and C strains.

FIG. 6 summarizes the results of a bactericidal assay testing anti-CHORI vaccine, anti-rNspA, and anti-Norwegian vaccine antisera against meningococcal B strain 2996.

FIG. 7 provides data showing the complement-mediated bactericidal activity of antisera and antibodies.

FIG. 8 provides data showing the complement-mediated bactericidal activity of antisera from mice immunized with the indicated vaccines.

FIG. 9 provides data showing the bactericidal activity of antisera from guinea pigs immunized with the indicated vaccines.

FIG. 10 provides data showing the passive protection in infant rats against meningococcal B strain 8047 bacteremia by antisera and antibodies.

FIG. 11 provides data showing the passive protection in infant rats against meningococcal B strain 8047 bacteremia by guinea pig antisera.

FIG. 12 is a photograph of a silver stained 15% SDS-PAGE gel of surface-exposed proteins precipitated by anti-CHORI antigen antisera from non-encapsulated meningococcal B strain M7. Lane 1, total protein from M7. Lane 2, proteins precipitated by murine anti-CHORI antisera. Lane 3, proteins precipitated by murine negative control antisera. The numbers on the left of the figure indicate apparent molecular mass in kDa.

FIG. 13 is a photograph of a Western blot of a 15% SDS-PAGE gel of surface-exposed proteins precipitated by anti-CHORI antigen antisera from non-encapsulated meningococcal B strain M7. Lanes 1 and 4, total protein from M7. Lanes 2 and 5, proteins precipitated by murine anti-CHORI antigen antisera. Lanes 3 and 6, proteins precipitated by murine negative control antisera. Anti-CHORI antigen antisera were used as the primary detecting antibody in lanes 1 to 3 and an anti-PorA mAb MN16C13F4 (Rijksinstituut Voor Volksgezondeid en Mileu, Biltoven, The Netherlands) that is specific for serosubtype P1.2 was used as the primary detecting antibody in lanes 4 to 5.

FIG. 14 provides data showing the bacterial surface accessible proteins precipitated by pooled antisera from mice sequentially immunized with MenC strain RM1090 MV, MenB strain BZ198 MV, and MenA strain Z1092 OMV.

FIG. 14A provides additional examples of data showing the bacterial surface accessible proteins precipiated by pooled anitsera from mice sequentially immunized with MenC strain RM1090 MV, MenB strain BZ198 MV, and MenA strain Z1092 OMV.

Figure 15:
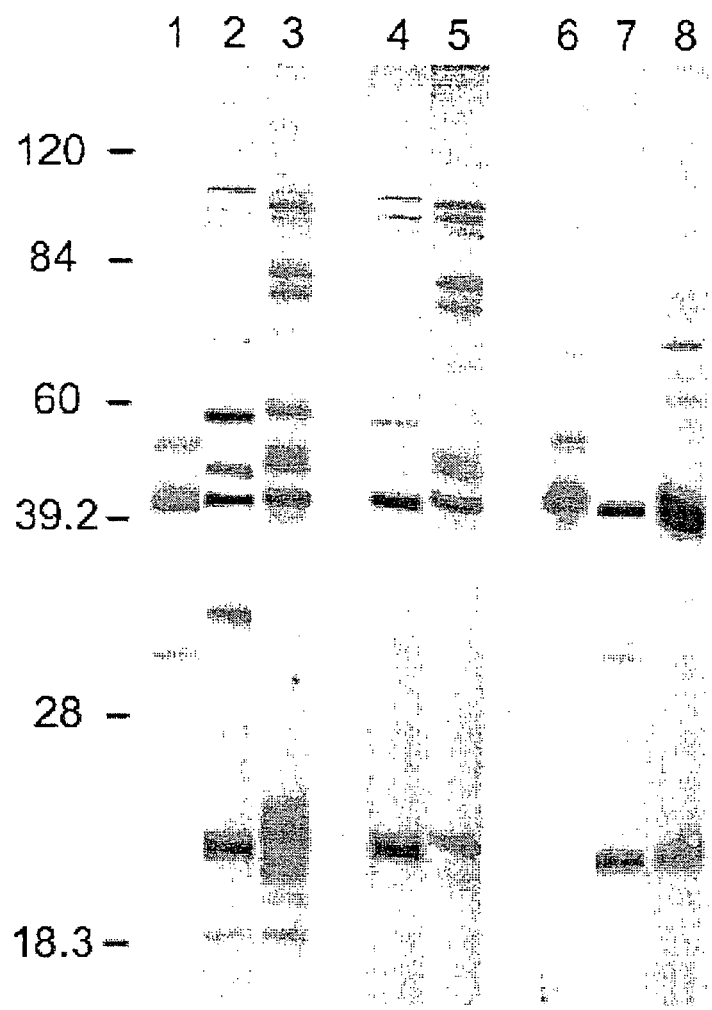

FIG. 15 is a photograph of a Western blot of a 15% SDS-PAGE gel of MV or OMV preparations. Primary detecting antisera is pooled mouse anti-CHORI/CFA vaccine antisera in lanes 1 to 3, pooled mouse anti-CHORI/$Al_2(OPO_3)_3$ in lanes 4 and 5, and pooled guinea pig anti-CHORI/$Al_2(OPO_3)_3$ in lanes 6 to 8. Lanes 1 and 6, MV proteins prepared from strain RM1090. Lanes 2, 4, and 7, MV proteins prepared from strain BZ198. Lanes 3, 5, and 8, OMV proteins prepared from strain Z1092. The numbers on the left of the figure indicate apparent molecular mass in kDa.

FIG. 16 provides data showing the apparent molecular masses of proteins from the indicated MV or OMV preparations that are reactive with antisera from mice and guinea pigs that were sequentially immunized with MV from MenC strain RM1090 and MenB strain BZ198, and OMV from MenA strain Z1092.

FIG. 17 provides data from ELISA showing the absorption of anti-LOS antibodies from pooled antisera obtained from mice and guinea pigs sequentially immunized with MV from MenC strain RM1090 and MenB strain BZ198, and OMV from MenA strain Z1092, or three injections of a mixture of the three vesicle preparations.

FIG. 18 provides data from complement-mediated bactericidal assay showing that the absorption of anti-LOS antibodies from pooled antisera obtained from mice and guinea pigs sequentially immunized with MV from MenC strain RM1090 and MenB strain BZ198, and OMV from MenA strain Z1092, or three injections of a mixture of the three vesicle preparations does not significantly change the bactericidal activity of the antisera against MenB strains that are homologous or heterologous to the vaccine strains.

FIG. 19 provides data from a whole cell ELISA showing examples of mAbs produced from mice sequentially immunized with MV from MenC strain RM1090 and MenB strain BZ198, and OMV from MenA strain Z1092. Several mAbs are reactive with all meningococcal strains tested and others react with a limited subset of strains.

FIG. 20 summarizes the complement-mediated bactericidal activity of mAbs prepared from mice immunized with anti-CHORI antigen and tested against several MenB strains.

FIG. 21 summarizes the meningococcal serotype and serosubtype defining monoclonal antibodies available from RIVM.

FIG. 22 summarizes the serogroup, serotype, and serosubtype defining monoclonal antibodies available from NIBSC.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antigen" includes a plurality of such antigens and reference to "the vesicle" includes reference to one or more vesicles and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Immunization of infants, older children and adults with meningococcal outer membrane vesicle (OMV) vaccines induces serum bactericidal antibodies, a serological correlate of protection against disease (Goldschneider et al, 1969, J. Exp. Med. 129:1307). The efficacy of OMV vaccines for prevention of meningococcal B disease also has been demonstrated directly in older children and adults in randomized, prospective clinical trials, and in retrospective case-control studies. See, e.g., results summarized in background section and in FIG. 1. Thus, the clinical effectiveness of outer membrane vesicle vaccines is not in dispute. Such vaccines are close to licensure for use in Norway in older children and adults, and are in late-stage clinical development for licensure in other European countries. An OMV vaccine prepared by the Finley Institute in Cuba also is available commercially and has been given to millions of children in South America.

The serum bactericidal antibody response to OMV vaccines tends to be strain specific (Tappero et al., 1999, *JAMA* 281:1520; and Rouupe van der Voort E R, 2000, Vaccine, 18:1334-1343). PorA is immunodominant, and the immunity induced is predominantly specific to the strains from which the membrane vesicles were obtained (Tappero et al., 1999, *JAMA* 281:1520; Martin S L et al, 2000, Vaccine, 18:2476-2481). This limitation is primarily because of antigenic variability of the PorA protein and is particularly true in infants who are immunologically naïve (Tappero et al.) with respect to prior exposure to *neisserial* antigens.

Hence, the present invention involves eliciting an immune response that is broadly reactive with diverse disease-producing *N. meningitidis* strains. The invention circumvents the problem of immunodominance of antigenically variable domains of PorA in vesicle- or PorA-based vaccines by focusing the antibody response on common antigens in the vaccine strains. Importantly, the methods of the invention elicit serum bactericidal antibody, the only proven serologic correlate of protection in humans (Goldschneider et al. 1969, supra) against strains of *Neisseria* expressing serosubtype epitopes that were not used in the vaccine preparations. Further, the method elicits serum bactericidal antibody against strains that are not killed by antibody to a conserved protein such as *Neisserial* surface protein A, a candidate meningococcal vaccine (Martin et al., 2000. J. Biotechnol. 83:27-31; Moe et al. (1999 Infect. Immun. 67: 5664; Moe et al. Infect Immun. 2001 69:3762). Without being held to theory, the vaccine and immunization regimen of the invention provides its unexpected advantages in broad spectrum protective immunity by eliciting antibodies that are specific for both conserved and non-conserved antigens.

A. Definitions

The term "protective immunity" means that a vaccine or immunization schedule that is administered to a mammal induces an immune response that prevents, retards the development of, or reduces the severity of a disease that is caused by *Neisseria meningitidis*, or diminishes or altogether eliminates the symptoms of the disease.

The phrase "a disease caused by a strain of serogroup B of *Neisseria meningitidis*" encompasses any clinical symptom or combination of clinical symptoms that are present in an infection with a member of serogroup B of *Neisseria meningitidis*. These symptoms include but are not limited to: colonization of the upper respiratory tract (e.g. mucosa of the nasopharynx and tonsils) by a pathogenic strain of serogroup B of *Neisseria meningitidis*, penetration of the bacteria into the mucosa and the submucosal vascular bed, septicemia, septic shock, inflammation, haemmorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischaemia, respiratory distress syndrome, pericarditis and meningitis.

The phrase "broad spectrum protective immunity" means that a vaccine or immunization schedule elicits "protective immunity" against at least one or more (or against at least two, at least three, at least four, at least five, against at least eight, or at least against more than eight) strains of *Neisseria meningitidis*, wherein each of the strains belongs to a different serosubtype as the strains used to prepare the vaccine. The invention specifically contemplates and encompasses a vaccine or vaccination regimen that confers protection against a disease caused by a member of serogroup B of *Neisseria meningitidis* and also against other serogroups, particularly serogroups A, C, Y and W-135.

The phrase "specifically binds to an antibody" or "specifically immunoreactive with", when referring to an antigen such as a polysaccharide, phospholipid, protein or peptide, refers to a binding reaction which is based on and/or is probative of the presence of the antigen in a sample which may also include a heterogeneous population of other molecules. Thus, under designated immunoassay conditions, the specified antibody or antibodies bind(s) to a particular antigen or antigens in a sample and do not bind in a significant amount to other molecules present in the sample. Specific binding to an antibody under such conditions may require an antibody or antiserum that is selected for its specificity for a particular antigen or antigens.

The phrase "in a sufficient amount to elicit an immune response to epitopes present in said preparation" means that there is a detectable difference between an immune response indicator measured before and after administration of a particular antigen preparation. Immune response indicators include but are not limited to: antibody titer or specificity, as detected by an assay such as enzyme-linked immunoassay (ELISA), bactericidal assay, flow cytometry, immunoprecipitation, Ouchter-Lowny immunodiffusion; binding detection assays of, for example, spot, Western blot or antigen arrays; cytotoxicity assays, etc.

A "surface antigen" is an antigen that is present in a surface structure of *Neisseria meningitidis* (e.g. the outer membrane, inner membrane, periplasmic space, capsule, pili, etc.).

The phrase "genetically diverse" as used in the context of genetically diverse strains of *Neisseria meningitidis*, refers to strains that differ from one another in the amino acid sequence of at least one, and usually at least two, more usually at least three polypeptides, particularly antigenic polypeptides. Genetic diversity of strains can be accomplished by selecting strains that differ in at least one or more, preferably at least two or more, of serogroup, serotype, or serosubtype (e.g., two strains that differ in at least one of the proteins selected from outer membrane, PorA and PorB proteins, are said to genetically diverse with respect to one another). Genetic diversity can also be defined by, for example, multi-locus sequence typing and/or multi-locus enzyme typing (see, e.g., Maiden et al., 1998, *Proc. Natl. Acad. Sci. USA* 95:3140; Pizza et al. 2000 Science 287:1816), multi-locus enzyme electrophoresis, and other methods known in the art.

"Serogroup" as used herein refers to classification of *Neisseria meningitides* by virtue of immunologically detectable variations in the capsular polysaccharide. About 12 serogroups are known: A, B, C, X, Y, Z, 29-E, W-135, H, I, K and L. Any one serogroup can encompass multiple serotypes and multiple serosubtypes.

"Serotype" as used herein refers to classification of *Neisseria meningitides* strains based on monoclonal antibody defined antigenic differences in the outer membrane protein Porin B. A single serotype can be found in multiple serogroups and multiple serosubtypes.

"Serosubtype" as used herein refers classification of *Neisseria meningitides* strains based on antibody defined antigenic variations on an outer membrane protein called Porin A, or upon VR typing of amino acid sequences deduced from DNA sequencing (Sacchi et al., 2000, *J. Infect. Dis.* 182: 1169; see also the Multi Locus Sequence Typing web site). Most variability between PorA proteins occurs in two (loops I and IV) of eight putative, surface exposed loops. The variable loops I and IV have been designated VR1 and VR2, respectively. A single serosubtype can be found in multiple serogroups and multiple serotypes.

"Enriched" means that an antigen in an antigen composition is manipulated by an experimentalist or a clinician so that it is present in at least a three-fold greater concentration by total weight, preferably at least 10-fold greater concentration, more preferably at least 100-fold greater concentration, and most preferably at least 1,000-fold greater concentration than the concentration of that antigen in the strain from which the antigen composition was obtained. Thus, if the concentration of a particular antigen is 1 microgram per gram of total bacterial preparation (or of total bacterial protein), an enriched preparation would contain at least 3 micrograms per gram of total bacterial preparation (or of total bacterial protein).

The term "immunologically naïve with respect to *Neisseria meningitidis*" denotes an individual (e.g., a mammal such as a human patient) that has never been exposed (through infection or administration) to *Neisseria meningitidis* or to an antigen composition derived from *Neisseria meningitidis* in sufficient amounts to elicit protective immunity, or if exposed, failed to mount a protective immune response. (An example of the latter would be an individual exposed at a too young age when protective immune responses may not occur. Molages et al., 1994, *Infect. Immun.* 62: 4419-4424). It is further desirable (but not necessary) that the "immunologically naïve" individual has also not been exposed to a *Neisserial* species other than *Neisseria meningitidis* (or an antigen composition prepared from a *Neisserial* species), particularly not to a cross-reacting strain of *Neisserial* species (or antigen composition). Individuals that have been exposed (through infection or administration) to a *Neisserial* species or to an antigen composition derived from that *Neisserial* species in sufficient amounts to elicit an immune response to the epitopes exhibited by that species, are "primed" to immunologically respond to the epitopes exhibited by that species.

B. Preparation of *Neisseria Meningitidis* Fractions and Detection of Antigens and Antigenic Compositions that Confer Protective Immunity 1. Antigenic Compositions The various antigenic compositions (e.g. lysed cells, subcellular fractions, MVs and OMVs, or individual antigens and combinations of antigens detected and isolated as described above and below) that are administered to an animal (especially a human patient) to induce an immune response are generally obtained by methods known in the art. In some embodiments, the antigen preparations used to elicit an immune response are prepared by culturing *Neisseria meningitidis* spp. using well-known bacterial culture techniques and preparing a fraction that contains antigens that induce protective immunity.

One preferred fraction comprises microvesicles (MV) or blebs that are released during culture of said *Neisseria meningitidis* spp. MVs may be obtained by culturing a strain of *Neisseria meningitidis* in broth culture medium, separating whole cells from the broth culture medium (e.g. by filtration, or by a low-speed centrifugation that pellets only the cells and not the smaller blebs, or the like), and then collecting the MVs that are present in the cell-free culture medium (e.g. by filtration, differential precipitation or aggregation of MVs, or by a high-speed centrifugation that pellets the blebs, or the like). Strains for use in production of MVs can generally be selected on the basis of the amount of blebs produced in culture (e.g., bacteria can be cultured in a reasonable number to provide for production of blebs suitable for isolation and administration in the methods described herein). An exemplary strain that produces high levels of blebs is described in PCT Publication No. WO 01/34642. In addition to bleb production, strains for use in MV production may also be selected on the basis of NspA production, where strains that produce higher levels of NspA may be preferable (for examples of *N. meningitides* strains having different NspA production levels, see, e.g., Moe et al. (1999 Infect. Immun. 67: 5664).

A second preferred fraction comprises outer membrane vesicles (OMV) prepared from the outer membrane of a cultured strain of *Neisseria meningitidis* spp. OMVs may be obtained from a *Neisseria meningitidis* grown in broth or solid medium culture, preferably by separating the bacterial cells from the culture medium (e.g. by filtration or by a low-speed centrifugation that pellets the cells, or the like), lysing the cells (e.g. by addition of detergent, osmotic shock, sonication, cavitation, homogenization, or the like) and separating an outer membrane fraction from cytoplasmic molecules (e.g. by filtration; or by differential precipitation or aggregation of outer membranes and/or outer membrane vesicles, or by affinity separation methods using ligands that specifically recognize outer membrane molecules; or by a high-speed centrifugation that pellets outer membranes and/or outer membrane vesicles, or the like); outer membrane fractions may be used to produce OMVs.

In the production of MVs or OMVs, it may be preferable to use strains that are relatively low producers of endotoxin (lipopolysaccharide, LPS) so as to decrease the need to remove endotoxin from the final preparation prior to use in humans. For example, the OMV and/or MV can be prepared from mutants of these *Neisseria* strains in which lipooligosaccharide or other antigens that may be undesirable in a vaccine (e.g. Rmp) is reduced or eliminated.

Where desired (e.g., where the strains used to produce MVs or OMVs are associated with endotoxin or particular high levels of endotoxin), the MVs or OMVs are optionally treated to reduce endotoxin, e.g., to reduce toxicity following administration. Reduction of endotoxin can be accomplished by extraction with a suitable detergent (for example, BRIJ-96, sodium deoxycholate, sodium lauoylsarcosinate, Empigen BB, Triton X-100, TWEEN 20 (sorbitan monolaurate polyoxyethylene), TWEEN 80, at a concentration of 0.1-10%, preferably 0.5-2%). Where detergent extraction is used, it is preferable to use a detergent other than deoxycholate. Extraction of OMV and MV preparations with deoxycholate resulted in removal of some non-capsular protein antigens (see FIG. 2). Vaccination of animals with OMV or MV preparations subjected to deoxycholate extraction elicited an immune response that was associated with lower titers of bactericidal antibodies compared to vaccination with non-deoxycholate-extracted material.

In addition to MVs or OMVs, isolated antigens or particular combinations of antigens may be used to induce a protective immune response. The identity of the isolated antigens or combinations of antigens are described below.

Immunogenic compositions used as vaccines comprise an immunologically effective amount of antigen, as well as any other compatible components, as needed. By "immunologically effective amount" is meant that the administration of that amount to an individual, either in a single dose or as part of a series, is effective for treatment or prevention. This amount varies depending upon the health and physical condition of the individual to be treated, age, the taxonomic group o individual to be treated (e.g., non-human primate, primate, etc.), the capacity of the individual's immune system to synthesize antibodies, the degree of protection desired, the formulation of the vaccine, the treating clinician's assessment of the medical situation, and other relevant factors. It is expected that the amount will fall in a relatively broad range that can be determined through routine trials. Dosage treatment may be a single dose schedule or a multiple dose schedule (e.g., including booster doses). The vaccine may be administered in conjunction with other immunoregulatory agents.

The antigen compositions or individual antigens to be administered are provided in a pharmaceutically acceptable solution such as an aqueous solution, often a saline solution, or they can be provided in powder form. The compositions may also include an adjuvant. Examples of known suitable adjuvants that can be used in humans include, but are not necessarily limited to, alum, aluminum phosphate, aluminum hydroxide, MF59 (4.3% w/v squalene, 0.5% w/v Tween 80, 0.5% w/v Span 85), CpG-containing nucleic acid (where the cytosine is ummethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic antigen.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (6) combinations of 3dMPL with, for example, QS21 and/oroil-in-water emulsions e.g. EP-A-0835318, EP-A-0735898, EP-A-0761231; (7) oligonucleotides comprising CpG motifs [Krieg Vaccine 2000, 19, 618-622; Krieg *Curr opin Mol Ther* 2001 3:15-24; Roman et al., *Nat. Med.*, 1997, 3, 849-854; Weiner et cu., *PNAS USA*, 1997, 94, 10833-10837; Davis et al, *J. Immunol,* 1998, 160, 870-876; Chu et al., *J. Exp. Med,* 1997, 186, 1623-1631; Lipford et al, Ear. *J. Immunol.,* 1997, 27, 2340-2344; Moldoveami et al., *Vaccine,* 1988, 16, 1216-1224, Krieg et al., *Nature,* 1995, 374, 546-549; Klinman et al., *PNAS USA,* 1996, 93, 2879-2883; Ballas et al, *J. Immunol,* 1996, 157, 1840-1845; Cowdery et al, *J. Immunol,* 1996, 156, 4570-4575; Halpern et al, *Cell Immunol,* 1996, 167, 72-78; Yamamoto et al, *Jpn. J. Cancer Res.,* 1988, 79, 866-873; Stacey et al, *J. Immunol.,* 1996, 157, 2116-2122; Messina et al, *J. Immunol,* 1991, 147, 1759-1764; Yi et al, *J. Immunol,* 1996, 157, 4918-4925; Yi et al, *J. Immunol,* 1996, 157, 5394-5402; Yi et al, *J. Immunol,* 1998, 160, 4755-4761; and Yi et al, *J. Immunol,* 1998, 160, 5898-5906; International patent applications WO96/02555, WO98/16247, WO98/18810, WO98/40100, WO98/55495, WO98/37919 and WO98/52581] i.e. containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g. a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+IM2 (optionally+a sterol) e.g. WO98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc The antigens may be combined with conventional excipients, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antigen in these formulations can vary widely, and will be selected primarily based on fluid volumes, viscosities, body weight and the like in accordance with the particular mode of administration selected and the patient's needs. The resulting compositions may be in the form of a solution, suspension, tablet, pill, capsule, powder, gel, cream, lotion, ointment, aerosol or the like.

The concentration of immunogenic antigens of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

2. Immunization

The MVs, OMVs, isolated antigens, or combinations of antigens of the present invention are administered orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980). Administration of the MVs, OMVs, isolated antigens, or combinations of antigens can be performed serially or as a mixture, as described in more detail below.

It is recognized that the polypeptides and related compounds described above, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

In order to enhance serum half-life, the antigenic preparations that are injected may also be encapsulated, introduced into the lumen of liposomes, prepared as a colloid, or other conventional techniques may be employed which provide an extended serum half-life of the peptides. A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028. The preparations may also be provided in controlled release or slow-release forms for release and administration of the antigen preparations as a mixture or in serial fashion.

The compositions are administered to an animal that is at risk from acquiring a *Neisserial* disease to prevent or at least partially arrest the development of disease and its complications. An amount adequate to accomplish this is defined as a "therapeutically effective dose." Amounts effective for therapeutic use will depend on, e.g., the antigen composition, the manner of administration, the weight and general state of health of the patient, and the judgement of the prescribing physician. Single or multiple doses of the antigen compositions may be administered depending on the dosage and frequency required and tolerated by the patient, and route of administration.

In particular embodiments, the antigen compositions described herein are administered serially. First, a therapeutically effective dose of a first antigen composition (e.g. MV, OMV, isolated antigen, or combinations of antigens, with or without excipients) prepared from a first *Neisserial* strain is administered to an individual. The first antigenic composition is generally administered in an amount effective to elicit a immune response (e.g., activation of B and/or T cells). Amounts for the initial immunization generally range from about 0.001 mg to about 1.0 mg per 70 kilogram patient, more commonly from about 0.001 mg to about 0.2 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration.

After administration of the first antigen composition, a therapeutically effective dose of a second antigen composition (e.g. MV, OMV, isolated antigen, or combinations of antigens, with or without excipients) prepared from a second *Neisserial* strain is administered to an individual after the individual has been immunologically primed by exposure to the first antigen composition. The booster may be administered days, weeks or months after the initial immunization, depending upon the patient's response and condition. The existence of an immune response to the first antigen composition may be determined by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like) and/or demonstrating that the magnitude of the immune response to the second injection is higher than that of control animals immunized for the first time with the composition of matter used for the second injection (e.g. immunological priming). Immunologic priming and/or the existence of an immune response to the first antigen composition may also be assumed by waiting for a period of time after the first immunization that, based on previous experience, is a sufficient time for an immune response and/or priming to have taken place—e.g. 2, 4, 6, 10 or 14 weeks. Boosting dosages of the second antigen composition are typically from about 0.001 mg to about 1.0 mg of antigen, depending on the nature of the immunogen and route of immunization.

In certain preferred embodiments, a therapeutically effective dose of a third antigen composition prepared from a third *Neisserial* strain is administered to an individual after the individual has been primed and/or mounted an immune response to the second antigen composition. The third booster may be administered days, weeks or months after the second immunization, depending upon the patient's response and condition. The existence of priming and/or an immune response to the second antigen composition may be determined by the same methods used to detect an immune response to the second antigen composition. The existence of priming and/or an immune response to the second antigen composition may also be assumed by waiting for a period of time after the second immunization that, based on previous experience, is a sufficient time for an immune response to have taken place—e.g. 2, 4, 6, 10 or 14 weeks. Boosting dosages of the second antigen composition are typically from about 0.001 mg to about 1.0 mg of antigen, depending on the nature of the immunogen and route of immunization. The present invention further contemplates the use of a fourth, fifth, sixth or greater booster immunization, using either a fourth, fifth or sixth strain of *Neisseria meningitidis* or any of the first, second, or third strains, or other strain that is genetically diverse with respect to at least one of the first, second, and third strains.

Where administration of antigenic compositions prepared from the first, second, and (optionally, but preferably) third strains is serial, the order of administration of the compositions can be varied. For example, the order of administration of OMV and/or Mv within these serial administration steps can be varied. For example, the following orders of administration are within the scope of the invention (from left to right, with the third administration being optional): OMV-OMV-OMV; OMV-OMV-MV; OMV-MV-MV; MV-MV-MV; MV-MV-OMV; MV-OMV-OMV; OMV-MV-OMV; and MV-OMV-MV. Preferably, the order of administration is MV-MV-OMV.

In other embodiments the first, second, and (optionally) third antigen compositions are administered as a mixture. In related embodiments, the first and second antigen compositions are administered as a mixture, and the third antigen composition is administered subsequently.

The mixtures is administered in an amount effective to elicit an immune response, particularly a humoral immune response, in the host. Amounts for the immunization of the mixture generally range from about 0.001 mg to about 1.0 mg per 70 kilogram patient, more commonly from about 0.001 mg to about 0.2 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration. The initial administration of the mixture can be followed by booster immunization of the same of different mixture, with at least one booster, more usually two boosters, being preferred.

In certain preferred embodiments, the first and second *Neisserial* strains are genetically diverse to one another, e.g., the strains belong to different PorB serotypes and/or PorA serosubtypes; and may also optionally belong to different capsular serogroups. Furthermore, the second and third *Neisserial* strains are genetically diverse to one antoher, e.g., the strains belong to different serotypes and/or serosubtypes;

may also optionally belong to different serogroups. The third *Neisserial* strain is preferably genetically diverse with respect to the first and second strains, but may, in some embodiments, not be genetically diverse with respect to the first strain. For example, the serotype and/or serosubtype of the third *Neisserial* strain should preferably be different from the first and second strain but it may be the same as the first strain.

The present invention also specifically contemplates that antigen compositions from other members of the genus *Neisseria* may be administered as described herein to generate protective immunity against *Neisseria meningitidis*. For example, *Neisseria lactamica*, a nonpathogenic non-encapsulated commensal member of the genus *Neisseria* that is commonly found in the human nasopharynx, encompasses strains which have many antigens present on *N. meningitidis* and, therefore, also may be used to prepare one of the immunogens envisioned in this invention. Thus, MVs and OMVs from the nonpathogenic *Neisseria lactamica* may be used to prime or elicit a protective immune response against *Neisseria meningitidis* (or against other pathogenic *Neisseria* such as *Neisseria gonorrhea*). This may be accomplished by initially administering an antigen composition (e.g., MV or OMV) from *Neisseria lactamica*, followed by administering a second and optionally a third antigen composition from *Neisseria meningitidis* (or *Neisseria gonorrhea*). The invention specifically contemplates also that antigen compositions from *Neisseria lactamica* strains be used for the initial, second and any subsequent administrations, wherein each lactamica strain has a different serotype and/or serosubtype as the others.

The invention also contemplates that the antigen compositions used at any step in the immunization protocol may be obtained from one or more strains of bacteria (especially *Neisseria lactamica* or *Neisseria meningitidis*) that are genetically engineered by known methods (see, e.g. U.S. Pat. No. 6,013,267) to express one or more nucleic acids that encode one or more molecules of interest, particularly molecules that elicit or enhance a protective immune response. The nucleic acids may, for example, encode Porin A, Porin B, NspA, pilin, or other *Neisserial* proteins. Other exemplary nucleic acids include those that encode *Neisserial* proteins immunoprecipitated with anti-sera produced following vaccination with the CHORI vaccine, particularly those proteins having apparent molecular masses of about 80 kDa, about 59.5 kDa, about 40.7 kDa. about 39.6 kDa, about 33 kDa, about 27.9 kDa, and 14.5 kDa, or antigenic fragments thereof. Further exemplary nucleic acids include those that encode *Neisserial* proteins detected by Western blot with anti-sera produced following vaccination with the CHORI vaccine, particularly those proteins having apparent molecular masses of about 53 kDa-57 kDa; about 46-47 kDa, about 33 kDa, about 20 kDa to 21 kDa; and about 18 kDa. The nucleic acids may encode any of the above proteins that is truncated, or altered to include or delete a glycosylation site, or to include or delete any epitope, or to increase the expression of any of the above proteins. Of particular interest are antigenic fragments of such proteins. In addition, the antigen compositions of the invention can comprise additional antigens of *N. meningiditis* such as those exemplified in PCT Publication Nos. WO 99/24578, WO 99/36544; WO 99/57280, WO 00/22430, and WO 00/66791, as well as antigenic fragments of such proteins.

An important aspect of the present invention is that the antigen compositions used to prime and boost a broad protective immunity against *Neisseria meningitidis* are prepared from strains of *Neisseria* that possess variant immunodominant antigens (the main antigens that are routinely detected by antisera from different host animals that have been infected with *Neisseria*; representative examples include Porin A, Porin B, pilin, NspA etc.). In the examples described in the Examples section below, the strains vary with respect to either PorA or PorB, as evinced by their serotype or serosubtype. The strains also may vary with respect to the capsule molecule, as reflected by their serogroup.

Serotype and serosubtype classification is currently determined by detecting which of a panel of known monoclonals, which are known to recognize specific Porin molecules, bind to an unknown strain (Sacchi et al., 1998, *Clin. Diag. Lab. Immunol.* 5:348, see Tables 8 and 9 for partial lists of monoclonals). It is probable that other such monoclonals will be identified. The use of any novel serotypes and serosubtypes which may be defined by any new monoclonals are specifically contemplated by the invention. In addition, serotypes and serosubtypes may be defined, not only by interaction with monoclonal antibodies, but also structurally by the absence and/or presence of defined peptide residues and peptide epitopes (Sacchi et al., 2000, *J. Infect. Dis.* 182:1169). Serotype and serosubtype classification schemes that are based on structural features of the Porins (known or that may be discovered at a later date) are specifically encompassed by the invention.

One purpose and effect of serial administration of antigen compositions from different strains is to potentiate an immune response to antigens and epitopes that are typically not immunodominant, particularly non-immunodominant epitopes that exhibit less genetic variability than the known immunodominant epitopes. The invention specifically encompasses the serial administration of antigen compositions from *Neisserial* strains that differ with respect to immunodominant antigens other than the Porins (e.g., phospholipids, polysaccharides, lipopolysaccharides, pilins, OmpA, Opa, Opc, etc.).

The antigen compositions are typically administered to a mammal that is immunologically naïve with respect to *Neisseria meningitidis*. In a particular embodiment, the mammal is a human child about five years or younger, and preferably about two years old or younger, and the antigen compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

In general, administration to any mammal is preferably initiated prior to the first sign of disease symptoms, or at the first sign of possible or actual exposure to *Neisseria*.

Where particular immunogenic peptides that give rise to protective immunity are identified as described above and below, these antigens may be directly administered instead of MVs or OMVs. Where the identified antigens are peptides, the DNA encoding one or more of the peptides of the invention can also be administered to the patient. This approach is described, for instance, in Wolff et al., *Science* 247: 1465-1468 (1990), as well as U.S. Pat. Nos. 5,580,859 and 5,589,466.

3. Detection of Immunogenic Antigens

Subcellular fractions such as MVs and OMVs contain many antigens that may give rise to an immune response (see, e.g., FIG. 2 which depicts an electrophoretic gel of several such fractions). However, not every antigen in a preparation may elicit either a humoral response or protective immunity against a disease caused by a *Neisseria meningitidis* spp. Thus, the present invention also relates to individual antigens and/or combinations of antigens that induce protective immunity. Another objective is to use the identified antigens to formulate antigen compositions that may be used to elicit protective immunity against a Neisserial disease.

Antisera or mAbs are obtained or produced from mammals that are induced by the methods of the present invention to exhibit protective immunity against a disease caused by a *Neisseria meningitidis* spp. The antisera or mAbs are used to detect their corresponding *Neisserial* antigens, and the these antigens identified and isolated based on their physicochemical properties (class of molecule: peptide, nucleic acid, etc.; molecular mass, charge, chemical composition, etc.) or amino acid sequence. The isolated antigens (or immunologically effective portions thereof) can then be administered to mammals, singly and/or in combination, as described above, or as recombinant proteins (or immunologically effective fragments thereof) to assess the extent to which they induce protective immunity. The present invention specifically contemplates serially administering antigens isolated from one strain or different strains of *Neisseria*, or administering such antigens in a mixture comprising one or more, usually two or more, more usually three or more, still more usually four to six or more antigens.

Exemplary *Neisserial* antigens suitable for administration as described may include, but are not necessarily limited to those proteins immunoprecipitated with anti-sera produced following vaccination with the CHORI vaccine, particularly those proteins having apparent molecular masses of about 80 kDa, about 59.5 kDa, about 40.7 kDa. about 39.6 kDa, about 33 kDa, about 27.9 kDa, and 14.5 kDa, or antigenic fragments thereof. The antigens administered may include at least one of these antigens, or may include a combination of these antigens (e.g., at least two, at least three, at least four, or more).

Further exemplary *Neisserial* antigens suitable for administration as described may include, but are not necessarily limited to those proteins detected by Western blot with antisera produced following vaccination with the CHORI vaccine, particularly those proteins having apparent molecular masses of about 53 kDa-57 kDa; about 46-47 kDa, about 33 kDa, about 20 kDa to 21 kDa; and about 18 kDa, or antigenic fragments thereof. The antigens administered may include at least one of these antigens, or may include a combination of these antigens (e.g., at least two, at least three, at least four, or more).

It should be noted that references made to molecular masses of proteins refer to apparent molecular mass as determined using SDS-PAGE under the conditions described. It will be readily apparent to the ordinarily skilled artisan upon reading the present specification that these apparent molecular masses may vary for the same protein between two different experiments (e.g., using different gels or different preparations, when isolated from two different strains (e.g., due to polymorphisms between strains due to amino acid substitutions, deletions, and/or insertions, post-translational modifications, and the like)), and further that different proteins may appear to have the same apparent molecular mass.

Antigens that elicit protective immunity are detected by known methods: for example, immunoassay, immunoprecipitation, affinity chromatography, Western blots, etc. Examples of such methods are described below.

(a) Detection of Antigens by Immunoassay

A variety of immunoassay formats are used to characterize antisera and antibodies specifically immunoreactive with a particular antigen or antigenic composition, and also to measure the strength of an immune response to a particular antigen or antigenic composition. The first step is generally producing antiserum or an antibody preparation that binds to the antigen or antigenic composition.

(1) Production of Immune Antisera and Specific Polyclonal or Monoclonal Antibodies Methods of producing polyclonal and monoclonal antibodies used in these assays are known to those of skill in the art. See, e.g., Coligan (1991), Current Protocols in Immunology, Wiley/Greene, NY; and Harlow and Lane (1989), Antibodies: A Laboratory Manual, Cold Spring Harbor Press, NY; Stites et al. (eds.) 1997 Medical Immunology 9th ed. McGraw-Hill Professional Publishing, New York, N.Y., and references cited therein; Goding (198.6), Monoclonal Antibodies: Principles and Practice (2d ed.) Academic Press, New York, N.Y.; and Kohler and Milstein (1975), *Nature,* 256: 495-497. For example, in order to produce antisera for use in an immunoassay, a composition that contains antigens from *Neisseria meningitidis* spp. is given alone or mixed with an adjuvant and injected into an animal of choice (e.g. a mouse, rat, rabbit, pig, goat, cow, horse, chicken, etc.) according to any of the protocols described herein.

The animal's immune response to the immunogen preparation is monitored by taking test bleeds and determining the titer of reactivity of serially diluted aliquots of serum to serially diluted aliquots of the antigenic composition. Polyclonal antisera with a titer of $10^4$ or greater are selected and tested for their cross reactivity against non-immunogenic controls, using a competitive binding immunoassay. Specific monoclonal and polyclonal antibodies and antisera will usually bind with a dissociation constant ($K_D$) of at least about 0.1 mM, more usually at least about 1 μM, preferably at least about 0.1 μM or better, and most preferably, 0.01 μM or better.

(2) Monoclonal Antibodies

In some instances, it is desirable to prepare monoclonal antibodies from various mammalian hosts, such as mice, rodents, primates, humans, etc. Description of techniques for preparing such monoclonal antibodies are found in, e.g., Stites et al. Supra, and references cited therein; Harlow and Lane, Supra; Goding Supra; and Kohler and Milstein. Supra. Summarized briefly, this method proceeds by injecting an animal with an immunogenic preparation. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host.

Other suitable techniques involve selection of libraries of recombinant antibodies in phage or similar vectors (see, e.g., Huse et al. (1989) *Science* 246: 1275-1281; Ward et al. (1989) *Nature* 341: 544-546; and Vaughan et al. (1996) *Nature Biotechnology* 14: 309-314).

(3) Immunoassays

Once an immune serum or a monoclonal antibody that recognizes one or more *Neisserial* antigens is obtained, it may be used to perform immunoassays. For a review of immunological and immunoassay procedures in general, see D. Stites and A. Terr, (eds.), Supra. Moreover, the immunoassays of the present invention can be performed in any of several configurations, which are reviewed extensively in ENZYME IMMUNOASSAY, E. T. Maggio, ed., CRC Press, Boca Raton, Fla. (1980); "Practice and Theory of Enzyme Immunoassays," P. Tijssen, in LABORATORY TECHNIQUES IN BIOCHEMISTRY AND MOLECULAR BIOLOGY, Elsevier Science Publishers B.V. Amsterdam (1985); and Harlow and Lane, supra, each of which is incorporated herein by reference.

For example, solid-phase ELISA immunoassays are routinely used to select monoclonal antibodies specifically immunoreactive with an antigen. See Harlow and Lane, Supra.

Immunoabsorbed and/or pooled antisera (or monoclonal antibodies) are also used in a direct or competitive binding immunoassay. The latter compares the binding of a second antigen composition (e.g. MVs, OMVs, isolated antigens or antigen compositions from an unknown or a known different Neisserial strain) to that of the reference antigen composition used to elicit protective immunity. In order to make this comparison in the competitive assay, the two antigen preparations are each assayed at a wide range of concentrations and the amount of each molecule required to inhibit 50% of the binding of the antisera to the immobilized reference antigen preparation is determined. If the amount of the second protein required is less than 10 times the amount of the reference peptide used to make the antibody, then the second protein is said to specifically bind to an antibody generated to the reference antigen preparation.

(b) Western Blots

Western blot analysis generally comprises separating sample products by gel electrophoresis on the basis of molecular weight, transferring the separated proteins to a suitable solid support (such as a nitrocellulose filter, a nylon filter, or derivatized nylon filter), and incubating the sample with labeling antibodies that specifically bind to the analyte protein. The labeling antibodies specifically bind to analyte on the solid support. These antibodies are directly labeled, or alternatively are subsequently detected using labeling agents such as antibodies (e.g. labeled sheep anti-mouse antibodies where the antibody to an analyte is a murine antibody) that specifically bind to the labeling antibody.

4. Purification of Immunogenic Antigens

The antigens can be isolated (separated from one or more molecules with which the antigen is associated in vivo) and purified (a purified antigen, e.g. a protein, preferably exhibits essentially a single band on an electrophoretic gel for each dissociable subunit of the antigen) and used to elicit protective immunity.

Individual antigens, especially proteins and peptide fragments thereof, can be purified by any of a variety of known techniques, including, for example, reverse phase high-performance liquid chromatography (HPLC), ion-exchange or immunoaffinity chromatography, separation by size, or electrophoresis (see, generally, Scopes, R. *Protein Purification*, Springer-Verlag, N.Y. (1982)). For example, antigens from *Neisseria meningitidis* spp. that are recognized by broad spectrum antisera obtained after serial injections of OMVs and/or MVs obtained from different *Neisseria meningitidis* spp. are obtained by using broad spectrum antisera to generate enriched antigen preparations. Isolated antigens may also be prepared by immunoprecipitating a fraction obtained from *Neisseria meningitidis* spp. The antigens may also be isolated by conjugating immune antisera or monoclonal antibodies to a column and performing affinity chromatography. The source of the antigens may be a whole cell lysate obtained by known methods, for example by sonication, or alternatively by exposure to an ionic or nonionic detergent, or the source may be MVs or OMVs from a *Neisserial* strain.

5. Peptide Antigens

Furthermore, once the identity of protein antigens and/or specific peptide epitopes is established, antigen preparations from *Neisseria meningitidis* spp. suitable for inducing protective immunity in the present invention can be generated by synthesizing peptides by conventional techniques, and injecting synthetic peptide preparations into a mammal. Techniques for peptide synthesis are well known in the art. See, e.g., Stewart and Young, *Solid Phase Peptide Synthesis* (Rockford, Ill., Pierce), 2d Ed. (1984) and Kent, 1988, *Annu. Rev. Biochem.* 57:957.

Alternatively, nucleic acid sequences which encode the particular polypeptide may be cloned and expressed to provide the peptide. Standard techniques can be used to obtain and screen nucleic acid libraries to identify sequences encoding the desired sequences (see Sambrook et al., *Molecular Cloning—A Laboratory Manual*, Cold Spring Harbor Laboratory, Cold Spring Harbor, N.Y., 1989), or nucleic acids that encode desired peptides may be synthesized by known methods. Fusion proteins (those consisting of all or part of the amino acid sequences of two or more proteins) can be recombinantly produced. In addition, using in vitro mutagenesis techniques, unrelated proteins can be mutated to comprise the appropriate sequences.

It will be understood that the immunogenic antigens of the present invention may be modified to provide a variety of desired attributes, e.g. improved pharmacological characteristics, while increasing or at least retaining substantially all of the biological activity of the unmodified peptide. For instance, the peptides can be modified by extending, decreasing the amino acid sequence of the peptide. Substitutions with different amino acids or amino acid mimetics can also be made.

The peptides employed in the subject invention need not be identical to those disclosed in the Examples section below (e.g., with respect to molecular weight), so long as the subject peptides are able to induce an immune response against the desired antigen molecule. Thus, one of skill will recognize that a number of conservative substitutions (described in more detail below) can be made without substantially affecting the activity of the peptide.

Single amino acid substitutions, deletions, or insertions can be used to determine which residues are relatively insensitive to modification. Substitutions are preferably made with small, relatively neutral moieties such as Ala, Gly, Pro, or similar residues. The effect of single amino acid substitutions may also be probed using D-amino acids. The numbers and types of residues which are substituted or added depend on the spacing necessary between essential contact points and certain functional attributes which are sought (e.g. hydrophobicity versus hydrophilicity). Increased immunogenicity may also be achieved by such substitutions, compared to the parent peptide. In any event, such substitutions should employ amino acid residues or other molecular fragments chosen to avoid, for example, steric and charge interference which might disrupt binding.

The substituting amino acids, however, need not be limited to those naturally occurring in proteins, such as L-α-amino acids, or their D-isomers. The peptides may be substituted with a variety of moieties such as amino acid mimetics well known to those of skill in the art. (See, e.g., U.S. Pat. No. 6,030,619)

The individual residues of the immunogenic antigenic polypeptides can be incorporated in the peptide by a peptide bond or peptide bond mimetic. A peptide bond mimetic of the invention includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, Peptides and Proteins*, Vol. VII (Weinstein ed., 1983). Several peptide backbone modifications are known. These include ψ[CH$_2$S], Ψ[CH$_2$NH], Ψ[CSNH$_2$], Ψ[NHCO], Ψ[COCH$_2$] and Ψ[(E) or (Z) CH CH]. The nomenclature used above follows that suggested by Spatola, above. In this context, Ψ indicates the absence of an amide bond. The structure that replaces the amide group is specified within the brackets.

Amino acid mimetics may also be incorporated in the peptides. An "amino acid mimetic" as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to illicit an immune response against the appropriate antigen. Amino acid mimetics may include non-protein amino acids, such as β-γ-δ-amino acids, β-γ-δ-imino acids (such as piperidine-4-carboxylic acid), as well as many derivatives of L-α-amino acids. A number of suitable amino acid mimetics are known to the skilled artisan; they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) *Ann. Repts. Med. Chem.* 24: 243-2526.

As noted above, the peptides employed in the subject invention need not be identical, but may be substantially identical, to the corresponding sequence of the target antigen. Therefore, the peptides may be subject to various changes, such as insertions, deletions, and substitutions, either conservative or non-conservative, where such changes might provide for certain advantages in their use. The polypeptides of the invention can be modified in a number of ways so long as they comprise a sequence substantially identical (as defined below) to a sequence in the target region of the antigen.

Alignment and comparison of relatively short amino acid sequences (less than about 30 residues) is typically straightforward. Comparison of longer sequences may require more sophisticated methods to achieve optimal alignment of two sequences. Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (USA) 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e. resulting in the highest percentage of sequence similarity over the comparison window) generated by the various methods is selected.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschuel et al. (1977) Nucleic Acids Res. 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra).

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 10, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Polypeptides encompassed by the invention typically comprise at least about 10 residues and more preferably at least about 15 residues, preferably from a domain of the antigen that is exposed to the immune system. In certain embodiments the peptides will not exceed about 50 residues and typically will not exceed about 30 residues.

The immunogenic peptides are conformationally constrained. Means for achieving this are well known in the art (see, e.g., Hruby and Bonner in *Methods in Molecular Biology, Volume 35: Peptide Synthesis Protocols*, Pennington and Dunn eds (Humana Press, Totowa, N.J., 1994). A preferred means for preparing conformationally constrained peptides is through cyclization. Any method commonly used to produce cyclized oligopeptides can be used to produce the peptides of the invention. For example, in certain embodiments the peptides will include cysteine residues at both termini, which allow the production of cyclic peptides through disulfide linkages. Treatment of such a peptide with an oxidizing agent such as oxygen, iodine or similar agent will produce a cyclic peptide which may be further purified using chromatographic or other methods of chemical purification. Construction of cyclic peptides can also be accomplished through thioether linkages. For instance, N-bromoacetyl-derivatized peptides can be reacted with sulfhydryl-containing residues, such as cysteine. Cyclization occurs by reaction of the free sulfhydryl of cysteine in the peptide with the bromoacetyl group to form a thioether linkage (Robey et al., *Anal. Biochem.* 177: 373-7 (1989) and U.S. Pat. No. 5,066,716).

Other methods of constructing cyclic peptides are known to those skilled in the art. These include side chain-side chain, side chain-main chain and main chain-main chain cyclizations. In addition, linkers can be used to join the amino and carboxyl termini of a peptide. The linker is capable of forming covalent bonds to both the amino and carboxyl terminus. Suitable linkers are well known to those of skill in the art and include, but are not limited to, straight or branched-chain carbon linkers, heterocyclic carbon linkers, or peptide linkers. The linkers may be joined to the carboxyl and amino terminal amino acids through their side groups (e.g. through a disulfide linkage to cysteine) or through the alpha carbon amino and carboxyl groups of the terminal amino acids.

For a general discussion of suitable methods for cyclization, see Hruby and Bonner in Methods in *Molecular Biology, Volume 35: Peptide Synthesis Protocols*, Pennington and Dunn eds (Humana Press, Totowa, N.J., 1994). For instance, cyclizations may include formation of carba analogs and thioethers (Lebl et al. in Peptides 1986 Proceedings of the 19th European Peptide Symposium pp. 341-344; Robey et al., *Anal. Biochem.* 177: 373-7 (1989) and U.S. Pat. No. 5,066, 716), bis-thioethers (Mosberg et al. *JACS* 107: 2986-2987 (1985)), azopeptides (Siemion et al. *Mol. Cell. Biochem.* 34: (1991)), and other cyclic structures, such as bridging structures (Charpentier, M., et al., *J. Med. Chem;* 32(6): 1184-1190 (1989), Thaisrivongs, S., et al., *J. Med. Chem.* 34(4): 127 (1991) and Ozeki, E., et al., *Int. J. Peptide Protein Res.* 34:111 (1989)). Cyclization from backbone-to-backbone positions may also be used.

Bridging is a special type of cyclization in which distant sites in a peptide are brought together using separate bridging molecules or fragments. Bridging molecules may include, for example, succinic anhydride molecules (Charpentier, B., et al., supra), and carboxymethylene fragments (Thaisrivongs, S., et al., supra). Bridging by metals can also be used (Ozeki, E., et al., supra).

In some embodiments, the peptides include two or more cystine residues. The cystines can be substituted or added within the peptide or at either terminus. The position of the cystines is not critical so long as disulfide linkages can form between them which allow the production of cyclic peptides. For example, treatment of such a peptide with an oxidizing agent such as oxygen, iodine or similar agent will produce a cyclic peptide which may be further purified using chromatographic or other methods of chemical purification.

Additional embodiments include peptides containing antigenic sequences of protein sequences that have been incorporated into independently folding peptides (Regan & DeGrado, 1988, *Science* 241:976; Mutter, 1988, *TIBS* 13:260; Kamtekar et al., 1993, *Science* 262:1680; Sieber & Moe, 1996, *Biochemistry* 35:181; Butcher & Moe, 1996, *Proc. Natl. Acad. Sci. USA* 93:1135; FitzGerald et al., 1998, *Biochemistry* 273:9951). The independently folding peptides may be naturally occurring or of de novo design.

Peptides capable of eliciting protective immunity similar to that of the CHORI vaccine might also be obtained by using monoclonal antibodies produced by immunization with CHORI antigen or the like to select molecular mimetics from phage display peptide libraries or other combinatorial libraries such as small molecules or nucleic acids.

In addition to use of peptides, antibodies raised against peptides of the invention can be used to inhibit inflammatory responses. Antibodies can be raised to the peptides of the present invention using techniques well known to those of skill in the art. Anti-idiotypic antibodies can also be generated. The following discussion is presented as a general overview of the techniques available; however, one of skill will recognize that many variations upon the following methods are known.

Frequently, the peptides and antibodies of the invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837, 3,850,752, 3,939,350, 3,996,345, 4,277,437, 4,275,149 and 4,366,241. Also, recombinant immunoglobulins may be produced. See Cabilly, U.S. Pat. No. 4,816,567; and Queen et al. (1989) *Proc. Nat'l Acad. Sci. USA* 86: 10029-10033.

6. Passive Immunity

Immunoprotective antibodies that recognize *Neisserial* epitopes can also be administered to an organism (e.g. a human patient) to induce passive immunity against a *Neisserial* disease, either to prevent infection or disease from occurring, or as a therapy to improve the clinical outcome in patients with established disease (e.g. decreased complication rate such as shock, decreased mortality rate, or decreased morbidity, such as deafness).

Antibodies administered to an organism other than the species in which they are raised are often immunogenic. Thus, for example, murine or porcine antibodies administered to a human often induce an immunologic response against the antibody. The immunogenic properties of the antibody are reduced by altering portions, or all, of the antibody into characteristically human sequences thereby producing chimeric or human antibodies, respectively.

Chimeric antibodies are immunoglobulin molecules comprising a human and non-human portion. More specifically, the antigen combining region (or variable region) of a humanized chimeric antibody is derived from a non-human source (e.g. murine), and the constant region of the chimeric antibody (which confers biological effector function to the immunoglobulin) is derived from a human source. The chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431 and 4,975,369). An alternative approach is the generation of humanized antibodies by linking the CDR regions of non-human antibodies to human constant regions by recombinant DNA techniques. See Queen et al., *Proc. Natl. Acad. Sci. USA* 86: 10029-10033 (1989) and WO 90/07861.

In one preferred embodiment, recombinant DNA vector is used to transfect a cell line that produces an antibody against a peptide of the invention. The novel recombinant DNA vector contains a "replacement gene" to replace all or a portion of the gene encoding the immunoglobulin constant region in the cell line (e.g. a replacement gene may encode all or a portion of a constant region of a human immunoglobulin, or a specific immunoglobulin class), and a "target sequence" which allows for targeted homologous recombination with immunoglobulin sequences within the antibody producing cell.

In another embodiment, a recombinant DNA vector is used to transfect a cell line that produces an antibody having a desired effector function (e.g. a constant region of a human immunoglobulin), in which case, the replacement gene contained in the recombinant vector may encode all or a portion of a region of an antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

In another embodiment, this invention provides for fully human antibodies. Human antibodies consist entirely of characteristically human polypeptide sequences. The human antibodies of this invention can be produced by a wide variety of methods (see, e.g., Larrick et al., U.S. Pat. No. 5,001,065). In one embodiment, the human antibodies of the present invention are produced initially in trioma cells (descended from three cells, two human and one mouse). Genes encoding the antibodies are then cloned and expressed in other cells, particularly non-human mammalian cells. The general approach for producing human antibodies by trioma technology has been described by Ostberg et al. (1983), *Hybridoma* 2: 361-367; Ostberg, U.S. Pat. No. 4,634,664, and Engelman et al., U.S. Pat. No. 4,634,666. Triomas have been found to produce antibody more stably than ordinary hybridomas made from human cells.

Methods for producing and formulation antibodies suitable for administration to a subject (e.g., a human subject) are well known in the art. For example, antibodies can be provided in a pharmaceutical composition comprising an effective amount of an antibody and a pharmaceutical excipients (e.g., saline). The pharmaceutical composition may optionally include other additives (e.g., buffers, stabilizers, preservatives, and the like). An effective amount of antibody is generally an amount effective to provide for protection against *Neisserial* disease or symptoms for a desired period, e.g., a period of at least about 2 days to 10 days or 1 month to 2 months).

7. Diagnostic Assays

The antigens or antibodies of the invention can also be used for diagnostic purposes. For instance, peptides can be used to screen pre-immune and immune sera to ensure that the vaccination has been effective. Antibodies can also be used in immunoassays to detect the presence of particular antigen molecules associated with *Neisserial* disease.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

A. Membrane Preparations

Strains for preparation of OMVS and MVs were selected on the basis of sergroup, serotype, and serosubtype. Strains to be used in the preparation of MVs were selected for relatively high levels of blebbing and expression of NspA (see Moe et al. (1999 Infect. Immun. 67: 5664). Exemplary strains used in preparation of OMVs and MVs have been deposited with the American Type Culture Collection (ATCC; see below). Strains that produce high levels of blebs, which strains are particularly useful in the MV production, can be selected or are known in the art (see, e.g., WO 01/34642).

The meningococcal strain frozen at −80° C. in aqueous ~2% skim milk (w/v) was subcultured on a commercial chocolate agar plate (Remel, Laztakas, K S). After overnight growth at 37° C. in 4% $CO_2$, several colonies were selected to inoculate ~7 ml of sterile Mueller-Hinton broth to an $OD_{620\,nm}$ of 0.1. The culture was incubated at 37° C., 4% $CO_2$ with rocking until the $OD_{620\,nm}$ reaches 0.6-0.8 (two to three hours). Two to three 7 ml starter cultures were then used to inoculate 500 ml of Mueller-Hinton broth. The larger culture was grown to an $OD_{620\,nm}$ of 0.9-1.0 at 37° C. with vigorous shaking. Phenol is added to the culture to a final concentration of 0.5% (w/v) and the mixture is left at 4° C. overnight to inactivate the bacteria. The cells were then pelleted by centrifugation (11,000×g) for 30 min. at 4° C. The cell pellets were frozen at −20° C. until used for preparation of outer membrane protein vesicles (OMV).

Microvesicles (MV) were harvested from the phenol-treated cell culture supernatant by adding solid ammonium sulfate (390 g/l final concentration) slowly with stirring. After the ammonium sulfate was added and completely dissolved, the mixture was left at 4° C. overnight. The precipitated MVs were then collected by centrifugation at 11,000×g for 30 min. The precipitated MV pellet was resuspended in 0.04 volume of PBS and centrifuged again at 16,000×g for 15 min. at 4° C. The pellet was discarded and the MVs, which remain in the supernatant, were collected by centrifugation at 100,000×g for 2 hrs. at 4° C. The final pellet was resuspended in 0.01 volume (i.e. 5 ml per 500 ml of culture) of water ("MV" vaccine preparation). Alternatively, the pellet was resuspended in 0.1M Tris.HCl, pH 8.6, containing 10 mM EDTA and 0.5% (w/v) sodium deoxycholate (~3 ml/500 ml cell culture). After stirring (30 min), the mixture was centrifuged (125,000×g, 2 hrs, 4° C.). The supernatant was discarded and the pellet resuspended in 1 ml of 3% sucrose ("DOC MV" vaccine preparation). The protein concentration of the MV and DOC MV preparations was determined by BCA assay (Pierce Chemical Co., Rockford, Ill.). The MV and DOC MV suspensions were then frozen on dry ice and stored at −20° C. until used for immunization.

Outer membrane vesicles (OMV) were prepared by the method of Zollinger et al. (1979 J. Clin. Invest. 63: 836-848). The frozen cell pellet was resuspended in 10 ml of 0.05 M Tris.HCl buffer, pH 7.4 containing 0.15 M NaCl and 0.01 M EDTA then heated to 56° C. for 30 min. followed by cooling on ice. The cell suspension was then sonicated on ice with several 15-second bursts using a microprobe sonifier (Branson, Danbury, Conn.). Cell debris was removed by centrifugation at 16,000×g for 15 min., and the outer membrane vesicles (OMVs) in the supernatant were obtained by ultra-centrifugation at 100,000×g for 2 hrs. at 4° C. The OMV pellet was resuspended in 2 ml of water ("OMV" vaccine preparation). Alternatively, the frozen cell pellet was resuspended in 0.1M Tris.HCl, pH 8.6, containing 10 mM EDTA and 0.5% (w/v) sodium deoxycholate. After stirring for 30 min. at ambient temperature, the mixture was centrifuged (20,000×g, 30 min., 4° C.). The supernatant was retained and the pellet was reextracted and centrifuged again with one third volume of the same buffer. The supernatants from both extractions were combined and centrifuged (125,000×g, 2 hrs, 4° C.). The supernatant was discarded and the pellet was resuspended in 5 ml of 3% sucrose ("DOC OMV" vaccine preparation). The OMV and DOC OMV vaccine preparations were frozen on dry ice, and stored at −20° C. until used for immunization. The protein concentration of the OMV and DOC OMV preparations was determined by BCA (Pierce Chemical Co., Rockford, Ill.).

B. Immunization Schedule

MV or OMV preparations were diluted in PBS and either mixed with an equal volume of complete Freund's adjuvant (CFA; Sigma Chemical Company, St. Louis, Mo.) or aluminum hydroxide (ALHYDROGEL™ 1.3% from Superfos Biosector, Frederikssund, Denmark), or aluminum phosphate (ALHYDROGEL™ that had been incubated with PBS buffer for at least 3 hrs). In some vaccine preparations, CpG nucleotides (5'-TCCATGACGTTCCTGACGTT-3' (SEQ ID NO:1) Chiron Corp., Emeryville, Calif.) were added to the aluminum phosphate/antigen mixture to a final concentration of 100 µg/ml as a second adjuvant. Mice were immunized by the IP (CFA) or SC (aluminum phosphate, aluminum hydroxide) routes with 100 µl containing between 5 to 25 micrograms of total protein of the MV prepared from the meningococcal strain RM1090.

At 3- to 4-week intervals two subsequent booster doses (5-25 micrograms/mouse) were given with either incomplete Freund's adjuvant (IFA), or aluminum hydroxide, or aluminum phosphate (prepared as described above) by the IP or SC routes, respectively, of first MVs prepared from meningococcal strain BZ198 and then OMVs prepared from meningococcal strain Z1092. The sequential immunization with three different meningococcal strains, which were genetically different with respect to their serogroup, serotype, and serosubtype and other antigens constitutes what is hereafter designated "CHORI vaccine". In a second experiment, another group of mice were immunized with CHORI vaccine as described above except that CpG oligonucleotides were not used as a second adjuvant and the experiment included mice that were given the CHORI vaccine combined with aluminum hydroxide adjuvant and mice that were given three injections of a mixture of the MV/OMV described above together with aluminum phosphate. In a third experiment, groups of guinea pigs were given either sequential immunizations with CHORI vaccine antigens or three injections of a mixture of CHORI vaccine antigens combined with aluminum phosphate.

C. SDS-PAGE and Western Blots

Protein preparations were analyzed using 15% SDS-PAGE as described by Laemmli (1970 Nature 227: 680-685) employing a Mini-Protean II electrophoresis apparatus (Bio-Rad, Richmond, Calif.). Samples were suspended in SDS sample buffer (0.06 M Tris.HCl, pH 6.8, 10% (v/v) glycerol, 2% (w/v) SDS, 5% (v/v) 2-mercaptoethanol, 10 micrograms/ml bromophenol blue) and optionally heated to 100° C. for 1 min. before loading directly onto the gel.

FIG. 2 shows a Coomassie-stained 15% SDS-PAGE gel of the proteins present in the MV of strain Z1092 (lane 2) or OMV preparations from strain Z1092 (lane 4), or the respective preparations after having been extracted with 0.5% (w/v) sodium deoxycholate (i.e. DOC MV [lane 3] and DOC OMV [lane 5]) as described by Fredricksen et al. (1991, NIPH Ann. 14: 67-79). The four corresponding preparations made from meningococcal strains BZ198 and RM1090 (are shown in lanes 6 to 13, respectively). Five proteins, PorA, PorB, Rmp, Opa, and Opc, are known to constitute the major outer membrane proteins of *Neisseria meningitidis*. All of the preparations appear to contain the major outer membrane proteins PorA and PorB (~39-42 kDa) and the opacity proteins, Opa and Opc (~28-31 kDa), although the apparent mass of the particular proteins and relative amounts were different in each preparation. The less distinct protein having an apparent mass of ~31-34 kDa in the DOC OMV preparations may be reduction modifiable protein (Rmp). In addition to these major outer membrane proteins, each MV and OMv preparation contains various other proteins in lesser amounts. In general, the minor proteins are more variable between strains and between MV compared to OMV preparations.

D. Antibody Binding to the Cell Surface

Binding of antibodies to the surface of live bacteria was determined by indirect fluorescence flow cytometry (Granoff et al., 1998, *J. Immunol.* 160: 5028-5036). Bacterial cells were grown to mid-log phase in Mueller-Hinton broth, harvested by centrifugation, and resuspended in blocking buffer (PBS containing 1% (w/v) bovine serum albumin (BSA) and 0.4% (w/v) sodium azide) at a density of $~10^8$ cells per ml. Dilutions of test or control antiserum (typically 1:20, 1:200, 1:2000) were then added and allowed to bind to the cells, which were maintained on ice for 2 hrs. Following two washes with blocking buffer, the cells were incubated with FITC-conjugated F(ab')2 fragment goat anti-mouse IgG (H+L) (Jackson Immune Research, West Grove, Pa.) for 1 hr. The cells were washed twice with blocking buffer then reacted with 0.25% formaldehyde in PBS buffer before analyzing the bacterial cells by flow cytometry.

Positive control antibodies included meningococcal-specific serotyping or serosubtyping monoclonal antibodies (MN2C3B, MN16C13F4, Rijksinstituut Voor Volksgezondheid en Mileu, Bilthoven, The Netherlands) and SEAM 12, an anti-polysaccharide monoclonal antibody that is specific for encapsulated serogroup B strains (Granoff et al., 1998, *J. Immunol.* 160:5028). The negative control consisted of a mouse IgG monoclonal antibody (VIG10) of irrelevant specificity and polyclonal sera from mice immunized with membrane proteins from *E. coli*. Antibodies used to define serogroup, serotype, and serosubtype are provided in FIGS. 20 and 21.

Figure 3:
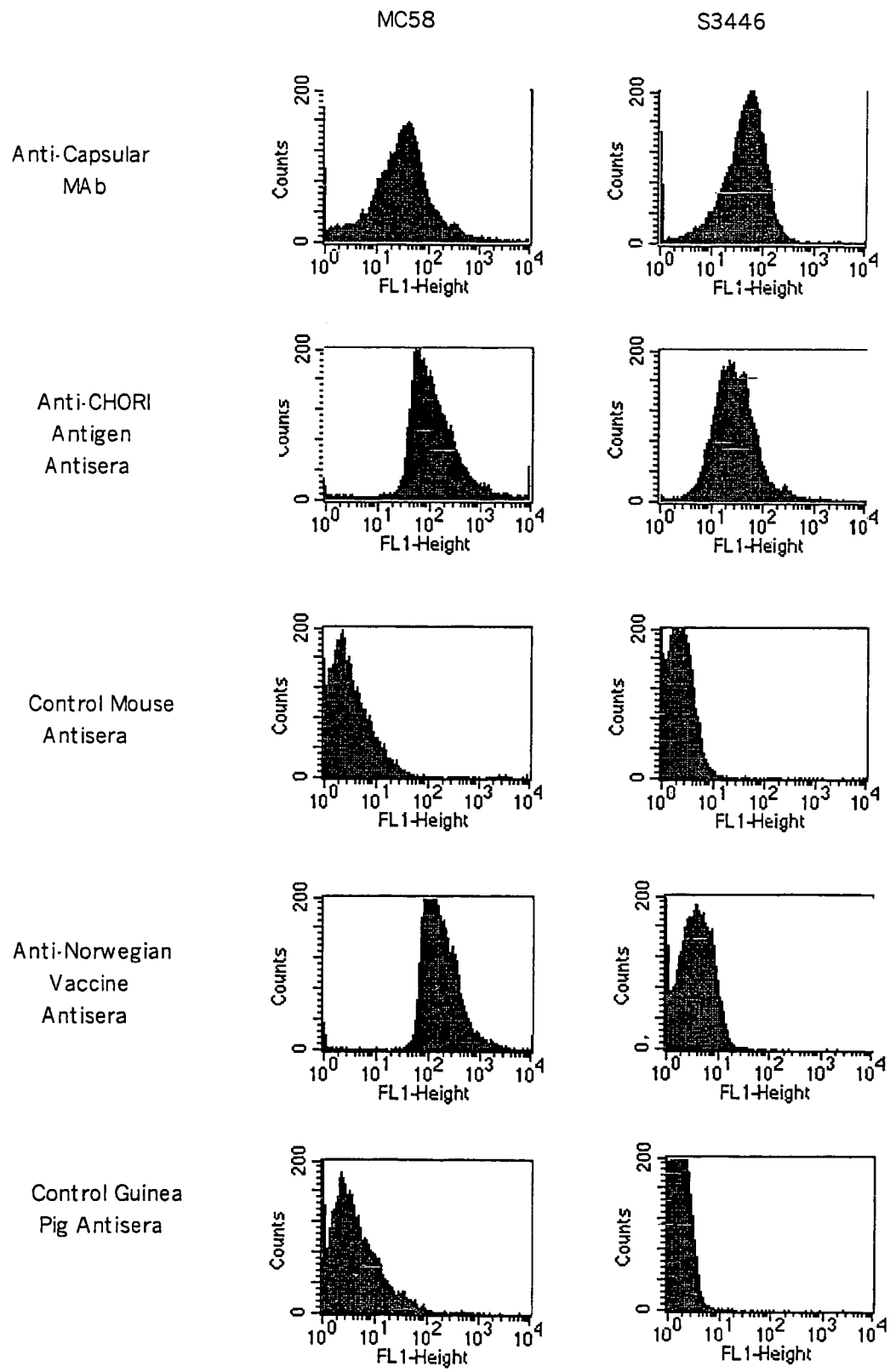

FIG. 3 shows the results of a typical experiment examining antibody binding to two test strains: MC58 and S3446. Both strains express PorA and PorB proteins that are heterologous with the respective porin protein s from the three strains used to prepare the CHORI vaccine. The antisera from mice immunized with CHORI antigen show an increase in fluorescence intensity with both strains when the antisera were tested at dilutions of 1:20 to 1:200. In contrast, polyclonal antisera prepared to proteins precipitated from culture supernatant of the *E. coli* show only low intensity background fluorescence (1:20 dilution), and were considered negative. Antisera from guinea pigs immunized with the Norwegian vaccine, prepared from OMV from strain H44/76 (P1.7,16), was positive against strain MC58 with an homologous PorA serosubtype (P1.7,16) but was negative when tested at 1:20 dilution against strain S3446 with a heterologous serosubtype (P1.22, 14).

As summarized in FIG. 4, of the 12 *N. meningitidis* serogroup B strains tested by flow cytometry, 11 (92%), including 6 strains with heterologous PorA serosubtypes, and 3 strains having both heterologous serotypes and serosubtypes, were positive for cell surface binding by anti-CHORI antigen antisera. The one negative strain does not express PorA, which suggests that some of the anti-CHORI vaccine antibodies bind to PorA or to proteins whose expression may be regulated in conjunction with PorA expression. In addition to the 11 meningococcal B strains, the anti-CHORI vaccine antisera was positive also in this assay when tested with heterologous meningococcal serogroup A (Z1073) and C (60E) strains (FIG. 5).

E. Complement-Dependent Bactericidal Antibody Activity

The bactericidal assay was adapted from the method previously described by Mandrell et al. (1995 *J. Infect. Dis.* 172: 1279-1289). Finding that a vaccine produces bactericidal antibodies against *Neisseria meningitidis* is accepted in the field as predictive of the vaccine's protective effect in humans (Goldschneider et al., 1969, *J. Exp. Med.* 129:1307; Borrow et al. 2001 Infect Immun. 69:1568). After overnight growth on chocolate agar, several colonies were inoculated into Mueller-Hinton broth (starting $A_{620 \, nm}$ of ~0.1) and the test organism was grown for approximately 2 hrs. to an $A_{620 \, nm}$ of ~0.6. After washing the bacteria twice in Gey's buffer containing 1% BSA (w/v), approximately 300 to 400 colony forming units (CFUs) were added to the reaction mixture. The final reaction mixture of 60 microliters contained 20% (v/v) complement, and serial 2-fold dilutions of test sera or control monoclonal antibodies in Gey's buffer. The complement source was human serum from a healthy adult with no detectable anticapsular antibody to serogroup B polysaccharide when tested by ELISA (Granoff et al., 1998, *J. Immunol.* 160: 5028-5036), and no detectable intrinsic bactericidal activity against the test strain at a final concentration of 20 or 40%.

In preliminary experiments with a panel of test sera, this complement source gave comparable bactericidal titers as those obtained with agammaglobulinemic serum as the complement source. Serum bactericidal titers were defined as the serum dilution (or antibody concentration) resulting in a 50% decrease in CFUs per ml after 60 min. incubation of bacteria in the reaction mixture, compared to the control CFU per ml at time 0. Typically, bacteria incubated with the negative control antibody and complement showed a 150 to 200% increase in CFU/mL during the 60 min. of incubation. FIG. 6 shows data from a typical experiment with meningococcal B strain 2996 tested with an anti-meningococcal B capsular mAb (SEAM 12, Granoff et al., 1998, *J. Immunol.* 160: 5028-5036), mouse and guinea pig control antisera, mouse anti-recombinant NspA and anti-CHORI antigen antisera, and guinea pig anti-Norwegian vaccine antisera.

FIG. 7 summarizes the results of measurement of complement-mediated bactericidal activity of the anti-CHORI antigen antisera to each of the menigococcal B strains tested. All 12 strains were killed by complement together with similar concentrations of a positive control anti-capsular mAb (SEAM 12; subtype IgG2a (Granoff et al., 1998, *J. Immunol.* 160: 5028-5036). Similarly, all 11 strains that were positive for anti-CHORI antisera binding by the flow assay were susceptible to antibody induced complement-mediated bacteriolysis (at a 1:10 dilution or higher, each showed greater than 50% killing, compared to CFU/ml present at time 0). Also, the heterologous meningococcal A and C strains that were positive when tested in the flow assay also were positive in the bactericidal assay (FIG. 5). Again, only strain M136, which does not express PorA, and was negative for antibody binding in the flow assay, was resistant to killing in the bactericidal assay. In contrast, antibodies elicited by either the Norwegian vaccine or rNspA, both of which are meningococcal B vaccine candidates currently being tested in humans, were able to activate complement-mediated bacteriolysis with only a limited number of the genetically diverse set of strains. As with the flow assay, the anti-NspA vaccine antisera and the anti-Norwegian vaccine antisera were bactericidal against only a limited number of the strains.

FIG. 8 summarizes the results of testing complement-mediated bactericidal activity of anti-CHORI antisera prepared in a second experiment in mice. Data are shown for antisera prepared with CHORI vaccine given with CFA or aluminum phosphate (without CpG). The results are shown for the 14 meningococcal B strains tested in this experiment (8 with serosubtypes heterologous to those of the vaccine strains). Results also are shown for one additional MenB strain in which the gene encoding NspA has been inactivated (BZ198ΔNspA). All 15 strains were killed by anti-CHORI antisera (14/15 with CHORI vaccine given with CFA; and 13/15 with CHORI vaccine given with aluminum phosphate; for the heterologous strains, 6/7 and 5/7, respectively). In contrast, only 1 of 15 strains was killed by antisera from control animals given 3 injections of *E. coli* MV. These results from a second experiment in mice confirm the earlier results obtained with the CHORI vaccine in experiment 1. In addition, the data indicate that the second adjuvant, CpG oligonucleotides, which was not used in the second experiment, is not needed by the CHORI vaccine to elicit broadly reactive antibody.

A group of mice in the second experiment received three injections, each consisting of a mixture of the same MV, MV and OMV used in the sequential immunization. The resulting antisera were bactericidal against 12 of the 15 strains (4 of 7 of the heterologous strains). Immunization with the mixture of antigens elicited broader bactericidal activity than expected but the titers measured against the some strains tended to be much lower than those obtained in animals given the sequential CHORI vaccine immunization (e.g. strains CU385 and 1000, titers of 1:128 and 1:128 after CHORI vaccine/alumunium phosphate vs. titers of <1:4 and 1:6 in antisera prepared against three injections of the mixed antigens/alumunium phosphate).

In a third experiment, groups of guinea pigs were immunized with CHORI vaccine given with aluminum phosphate (without CpG), or aluminum hydroxide (without CpG) The results are shown in FIG. 9 for 9 meningococcal B strains tested (5 with serosubtypes heterologous to those of the vaccine strains), and for one additional MenB strain in which the gene encoding NspA has been inactivated (BZ198ΔNspA). 9 of the 10 strains were killed by anti-CHORI antisera vs. 0 of 10 strains killed by antisera from control animals given 3 injections of *E. coli* MV. Thus the CHORI vaccine elicits broad-based bactericidal antibody responses in guinea pigs, a second animal model that may be more predictive of protective antibody responses in humans than mice.

F. Passive Animal Protection

A criticism of bactericidal assays is that it tests the activity of antibodies against bacteria grown in broth, and that bacteria grown in vivo may have different properties. Therefore, the ability of mouse anti-CHORI antiserum to confer passive protection against *N. meningitidis* group B bacteremia was tested in infant rats challenged IP, using an art-accepted model and method adapted from Saukkonen et al. (*J. Infect. Dis.*, 1988, 158: 209-212), which is regarded in the field as being predictive of results in humans. The meningococcal B strain 8047, which was positive by the flow cytometric assay for CHORI antigen-surface accessible epitopes and susceptible to anti-CHORI antigen bactericidal activity, was selected for this study. Infant pups (6- to 7-day old) from six litters of outbred Wistar rats (Charles River, Hollister, Calif.) were randomly redistributed to the nursing mothers. Groups of five to six animals were challenged IP with 100 µl of approximately $5 \times 10^3$ CFU of the group B strain 8047. The strain used had been passaged three times in infant rats. The bacteria isolated from blood cultures after the third pass was grown on chocolate agar overnight and stored frozen at −70° C. in vials containing sterile skim milk. On the day of the experiment, the bacteria were grown, washed and resuspended in PBS buffer containing 1% BSA, as described above for the bactericidal assay.

The animals were given antisera or antibodies diluted in PBS containing 1% BSA by IP injection 2 hrs. prior to bacterial challenge. Eighteen hours after the bacterial challenge, blood specimens were obtained by puncturing the heart with a syringe and needle containing one to two drops of 25 Units/ml of heparin without preservative (Fujisawa USA, Deerfield, Ill.). Aliquots of 1, 10 and 100 microliters of blood were plated onto chocolate agar. The CFU per ml of blood was determined after overnight incubation of the plates at 37° C. in 5% $CO_2$.

FIG. 10 summarizes the results of quantitative bacterial cultures performed on blood specimens obtained 18 hrs. after challenge. A dose of 10 micrograms per rat of the positive control anticapsular antibody, SEAM 3, was completely protective against the strain as was mouse anti-CHORI antisera at a dilution of 1:20. In contrast, the guinea pig anti-Norwegian vaccine antisera (1:20) and the two control sera (mouse antisera prepared to—*E. coli* proteins or guinea pig antisera from animals immunized with alum alone) were not able to protect against bacteremia caused by strain 8047.

In a second passive protection experiment using the protocol described above, anti-CHORI vaccine antisera prepared in guinea pigs were also shown to protect infant rats from meningococcal B bacteremia after IP challenge (FIG. 11). Protection was observed in animals treated with antisera prepared to vaccine administered with aluminum phosphate or aluminum hydroxide, and was superior to the protection observed in control animals treated with 20 µg of a murine anticapsular monoclonal antibody (SEAM 3).

G. Immunoprecipitation of Surface Antigens Recognized by Anti-CHORI Antigen Antibodies The method used for immunoprecipitation of surface-accessible antigens was based on those described by Hansen et al. (1981 *Infect. Immun.* 33: 950-953) and Gulig et al. (1982 *Infect. Immun.* 37: 82-88). In our studies, the method was used with either unlabeled cells, or with cells in which the surface proteins had had been radioiodinated. Cells were grown in Mueller-Hinton broth (~7 ml) to an OD of 0.6 and harvested by centrifugation at 5000×g at 4° C. The cell pellet was washed two times in cold PBS containing 1% BSA or, for the radioimmunoprecipitation assay, PBS alone.

Cells to be iodinated were transferred to a glass tube. One nanomole of KI and 1 mCi of $Na^{125}I$ (Amersham,) were added to the cell suspension. Radioiodination was initiated by the addition of 0.03% $H_2O_2$ (50 µl) and lactoperoxidase (Sigma, St. Louis, Mo.) in water (50 µl of a 1 mg/ml solution). The same amounts of $H_2O_2$ and lactoperoxidase were added at 4 min. intervals for 12 min. The reaction was terminated after 16 min. by adding the reaction mixture to cold PBI (20 ml) (i.e. NaI substituted for NaCl in PBS). The cells were harvested by centrifugation (5,000×g, 10 min, 4° C.), washed 2 times with PBS, then used immediately.

The cells were resuspended in PBS (2 ml) containing 1% BSA. The antisera were added to 0.5 ml aliquots of cell suspension. The mixture was incubated with rocking for 90 min. at 4° C. The cells were then collected by centrifugation (1 min. spin in microfuge), washed two times with PBS/1% BSA, and resuspended in 1 ml of solubilization buffer (50 mM Tris buffer, pH 7.8, containing 150 mM NaCl, 1 mM EDTA, 1% Triton X-100, 0.2% sodium deoxycholate, and 0.1% sodium dodecyl sulfate. After incubation for 60 min. at 37° C., the insoluble material was removed by centrifugation (45,000×g for 60 min. at 20° C.). The supernatants were then transferred to tubes containing 3-4 milligrams of protein A Sepharose beads (Sigma) pre-equilibrated with 50 µl of PBS. The samples were incubated overnight at 4° C. with rocking. The beads were washed five times with solubilization buffer. Bound proteins were released from the beads by adding 75 µl of SDS sample buffer and heated to 100° C. for 1 min. After removing the supernatant, 1 µl of 2-mercapto ethanol was added to each sample and then heated again to 100° C. for 1 min. The samples were then run on a 15% SDS-PAGE gel and stained using silver stain (Pierce Chemical Co., Rockford, Ill.).

For Western blots, the gel was equilibrated with buffer (48 mM Tris.HCl, 39 mM glycine, pH 9.0, 20% (v/v) methanol) and the proteins were transferred to a nitrocellulose membrane (Bio-Rad) using a Trans-Blot™ (Bio-Rad) semi-dry electrophoretic transfer cell. The nitrocellulose membranes were blocked with 2% (w/v) skim milk in PBS containing 0.2% (w/v) sodium azide. Antisera were diluted in the same blocking buffer containing 0.1% Tween-20. Bound antibody was detected using rabbit anti-mouse IgG,A,M-alkaline phosphatase conjugate polyclonal antibody (Zymed, South San Francisco, Calif.) diluted in PBS containing 1% (w/v) BSA, 1% (w/v) Tween-20, and 0.2% (w/v) sodium azide and Sigma Fast™ BCIP/NBT substrate (Sigma).

Figure 12:
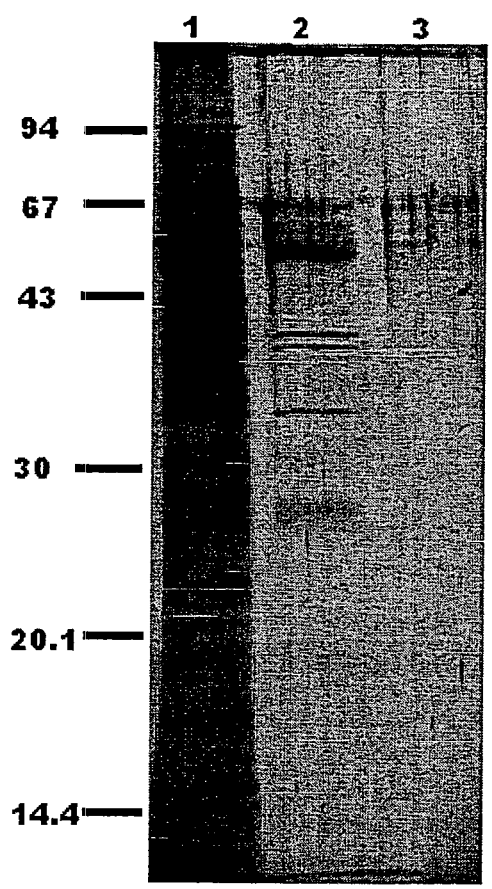

FIG. 12 is a silver-stained SDS gel demonstrating cell surface proteins precipitated with the anti-CHORI antisera (Lane 2) from M7, a non-encapsulated mutant of serogroup B strain, NMB (Stephens et al. 1991, Infect. Immun. 59: 4097-4107). six proteins having apparent masses of 59.5, 40.7. 39.6, 33, 27.9, and 14.5 kDa were precipitated by the antisera prepared to the CHORI antigen (Lane 2) but not by control anti-E. coli protein antisera (Lane 3). The same results were obtained when the anti-CHORI antigen antisera were used to precipitate surface proteins from the encapsulated parent strain, NMB (data not shown). Except for the 59.5 and 27.9 kDa heavy and light chain Ig proteins (see below), the same surface proteins detected by silver staining were observed also in $^{125}$I-labeled cells (data not shown).

Of note, there was no lipooligosaccharide (LOS), which would be detected by silver staining, that was precipitated by the anti-CHORI antigen antisera. Further experiments, described below, were designed to determine whether the observed surface binding and protective biological activity of anti-CHORI vaccine antisera were due to anti-LOS antibodies.

Figure 13:
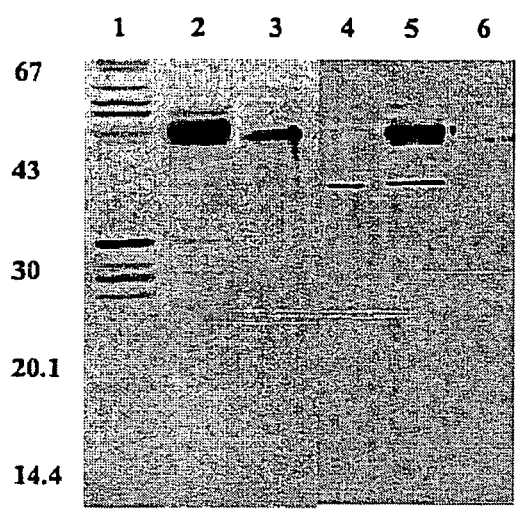

FIG. 13 shows a Western blot of the same samples as resolved on the SDS gel in FIG. 12. Samples in lanes 1 to 3 were detected by anti-CHORI vaccine antisera. Samples in Lanes 4 to 6 were detected by an anti-PorA P1.2-specific mAb. The proteins having apparent masses of 59.5 and 27.9 kDa in FIG. 13, (Lanes 2, 3, 5, and 6) correspond to antibody heavy and light chains, respectively, as they were detected with the rabbit anti-mouse Ig alkaline phosphatase conjugate secondary antibody. The 40.7 kDa protein precipitated by the anti-CHORI antigen antisera (FIG. 12, Lane 2) was reactive with the anti-PorA P1.2-specific antibody in the Western (FIG. 13, Lane 5) and is, therefore, PorA P1.2. As expected, PorA P1.2 also was detected in the total protein from M7 (FIG. 13, Lane 4). The anti-CHORI vaccine antisera detected only the 33 kDa protein (Lane 2) and not PorA. Thus, the antisera prepared to the CHORI antigen reacts with both native and denatured 33 kDa protein but only native forms of the 40.7. 39.6, and 14.5 kDa proteins present on the cell surface of strain M7 (FIG. 12, lane 2).

Similar immunoprecipitation experiments were performed on the MV and OMV preparations used for immunization and seven genetically diverse, encapsulated serogroup B strains. The results are summarized in FIG. 14. When the results are compared, it is apparent that the sequential immunization with membrane vesicles from three genetically diverse meningococcal strains elicits antibodies that recognize a variety of antigens. Some of the antigens that are recognized are the same in all strains; others are strain specific or common to subsets of strains. For example, proteins having apparent masses of 37-41 kDa were precipitated from strains BZ198 and NMB but not from any of the other strains. Similarly, proteins having an apparent mass of 25.7 kDa were precipitated from strains NG3/88 and S3446 but not from any other strains. However, there is one surface protein having an apparent mass of 32 to 33 kDa that is recognized by anti-CHORI antigen antisera in all of the examples except for strain M136, which was negative in both the flow and bactericidal assays. The 32 to 33 kDa protein may be a conserved antigen.

Additional experiments were performed on encapsulated serogroup B strains. CU385, BZ198 and 1000 using cells in which the surface proteins had had been radioiodinated (FIG. 14A) and precipitated with immune antisera from different groups of mice given the CHORI vaccine. In addition to the proteins described above, in this second set of experiments, proteins with apparent molecular masses between 10 and 14.5 kDa, and 80 kDa were precipitated from strains CU385 and BZ198. Three proteins with apparent kDa of 26, 41 and 45 were precipitated from strain 1000.

It is important to note that not all antigens recognized by the antisera from mice immunized with CHORI antigen were immunoprecipitated from the bacterial cells. There were also antibodies in the antisera to some antigens (e.g. the NspA protein) that were shown to be present by an ELISA or Western blot, but were not immunoprecipitated in this experiment. The failure to detect these other antigens may result from the fact that the antibody/antigen complex must be stable in the presence of detergents (Triton X-100, deoxycholate, and lauryl sulfate) to be detected.

H. Detection of Proteins Reactive in CHORI Vaccine MV and OMV Preparations with Anti-CHORI Vaccine Antibodies Elicited in Mice and Guinea Pigs FIG. 15 shows a Western blot of MVs from strains RM1090 (C:2a:P1.5,2:L3,7), and BZ198 (B:NT:P1.4) and OMV from strain Z1092 (A:4:P1.10). Antisera from mice immunized CHORI vaccine combined with CFA, or given with aluminum phosphate adjuvant, or from guinea pigs immunized with CHORI vaccine together with aluminum phosphate adjuvant, were used as the primary detecting antibody. The blot shows that the CHORI vaccine elicits antibodies that are reactive with several proteins having similar apparent molecular mass in each of the MV or OMV preparations independent of the animal species or adjuvant used in the vaccine. The apparent molecular masses of all proteins in the MV or OMV preparations that are reactive with anti-bodies produced by immunization with CHORI vaccine are summarized in FIG. 16.

I. Detection of Anti-LOS Antibody Activity

One of the antigenic determinants on the surface of the meningococci that has been observed to elicit bactericidal antibodies is lipooligosaccharide (LOS). In order to determine whether anti-LOS antibodies were elicited by the CHORI vaccine, a LOS affinity column was prepared and used to absorb out anti-LOS antibodies in the anti-CHORI vaccine antisera using methods described by Shenep et al. (1982, J. Infect. Dis. 145: 181-190) with the following modifications. LOS was prepared from each vaccine strain by the method of Appicella et al. (Bacterial Pathogensis (1997) V. L.

Clark and P. M. Bavoil eds. Academic Press, San Diego, Calif.), and was conjugated to BSA as follows. LOS (1 mg) was combined with BSA (2 mg) in 100 mM MES buffer, pH 5.0. EDC (1-ethyl-3-(3-dimehtylaminopropyl) carbodiimide HCl; 100 µl of a 10 mg/ml solution in water) was added with stirring followed by incubation at ambient temperature for 2 hrs. An equal mixture of the three-LOS-BSA conjugates (1 mg LOS-BSA conjugate per ml of hydrated gel) was coupled to CNBr-activated agarose beads (Sigma Chemical Co., St. Louis, Mo.) in sodium carbonate buffer (0.1 M, pH 8.0) overnight at ambient temperature.

After removal of anti-LOS antibodies by passing the anti-CHORI vaccine and anti-CHORI mixed antigen antisera through the LOS affinity column, the antisera were concentrated to their original volume by ultrafiltration and tested for the presence of anti-LOS antibody by ELISA and complement-mediated bactericidal activity against two MenB strains (BZ198 and S3032). As summarized in FIG. 17, the presence of anti-LOS antibody was greatly reduced or eliminated by absorption with the LOS-BSA conjugate affinity column. As shown in FIG. 18, there was little or no difference in the bactericidal titers between the absorbed and unabsorbed sera from mice or guinea pigs immunized with CHORI vaccine indicating that anti-LOS antibody does not contribute significantly to the bactericidal activity against either a vaccine strain (BZ198) or strain S3032, which has PorA and PorB that are heterologous to the strains used to prepare the vaccine. There was a greater effect on the bactericidal titers of antisera prepared from mice and guinea pigs immunized with Mixed CHORI vaccine indicating a more significant contribution of anti-LOS antibodies to the bactericidal titer in this antisera.

J. Preparation of Monoclonal Antibodies

Female CD1 mice (Charles River, Hollister, Calif.) were vaccinated sequentially with MV prepared from meningococcal strain RM1090 (C:2a:P1.5,2), BZ198 (B:NT:7,4), and OMV from strain Z1092 (A:4,21:P1.10). The mice were given three 100 microliters injections, each separated by three weeks, containing 5 micrograms of protein. The first two doses were given subcutaneously together with aluminum phosphate (0.5% wt/vol) and the final dose Was given without adjuvant and administered intraperitoneally (i.p.). Three days later, the animals were sacrificed and their spleen cells were fused with myeloma cells (P3×63-AG8.653) at a ratio of 1 spleen cell to 1.7 myeloma cell. After two weeks incubation in HAT selective medium, hybridoma supernatants were screened for antibody binding activity by whole cell ELISA using encapsulated MenB strains 1000 and CU385 as the target antigen. The method described by Abdillahi and Poolman, (Microb Pathog. 1988 4:27-32) was used for the whole cell ELISA assay. Hybridomas secreting antibody that was reactive with both 1000 and CU385 strains in a whole cell ELISA and were positive for binding by flow cytometry were cloned by limiting dilution and then expanded and frozen for subsequent use in tissue culture.

Antibodies from eight cell lines were characterized in detail. The subclasses of the monoclonal antibodies were determined using an antibody capture ELISA and alkaline phosphatase-conjugated polyclonal antibody specific for each of the mouse IgG subclasses, IgM, IgA, and κ and λ light chains (Southern Biotechnology Associates, Inc. Birmingham, Ala.). The monoclonal antibodies produced by the hybridoma clones were harvested from tissue culture media by ammonium sulfate precipitation (55% wt/vol). The concentration of the purified mAb was determined by capture ELISA using Ig standards as recommended by the manufacturer (Southern Biotechnology Associates, Inc. Birmingham, Ala.).

K. Reactivity of Anti-CHORI Antigen mAbs with Diverse MenB Strains

The ability of mAbs prepared from mice immunized with anti-CHORI antigen (administered with CFA or aluminum phosphate) to bind to diverse MenB strains was determined by whole cell ELISA (Abdillahi and Poolman, Microb Pathog. 1988 4:27-32). The results are summarized in FIG. 19. None of the monoclonal antibodies react with LOS prepared from the immunizing strains. The mAbs 1D9 and 14C7 are reactive with antigens in all or nearly all meningococcal strains tested but not with any non-neisserial strains. The mAb 14C7 is specific for the highly conserved *Neisserial* surface protein NspA since it is reactive with rNspA expressed in *E. coli*. This mAb also is reactive with strains 8047 and BZ198 but is not reactive with the corresponding strains in which the NspA gene has been inactivated. In contrast to the broadly reactive antibodies, antigens recognized by the mAbs 4B11 and 9B6 are limited to certain strains. Note that MAb 4B11 is reactive with strain 8047 but not with the corresponding 8047 mutant in which the NspA gene has been inactivated. However, mAb 4B11 does not bind to rNspA expressed in *E. coli* vesicles, and also does not bind to strain BZ198, which is known to naturally overexpress (see Moe et al. (1999 Infect. Immun. 67: 5664; Moe et al. Infect Immun. 2001 69:3762). Therefore, mAb 4B11 may recognize a NspA epitope that is specific to strain 8047, or an epitope on another membrane protein that is not present in strain BZ198 but is present and associated with NspA expression in strain 8047. Taken together, the results with the different mAbs show that the anti-CHORI antigen vaccine elicits antibodies against both highly conserved and non-conserved proteins.

L. Bactericidal Activity of Anti-CHORI Antigen mAbs with Diverse MenB Strains

The complement-mediated bactericidal activity of mAbs prepared from mice immunized with anti-CHORI antigen and tested against several MenB strains is summarized in FIG. 20. The monoclonal antibody 1D9, which reacts by ELISA with all *N. meningitides* strains tested, was not bactericidal. The monoclonal antibody 14C7, which appears to recognize NspA, was bactericidal or bacteriostatic against all strains tested except BZ198ΔNspA (a knockout of NspA). The activity of the 14C7 monoclonal antibody was superior to that of the control monoclonal antibody AL12 (produced in mice immunized with recombinant NspA (see Moe et al. Infect Immun. 2001 69:3762). This observation suggests that immunization with the CHORI vaccine provides a superior means for eliciting bactericidal anti-NspA antibodies as compared to immunization with a recombinant NspA-based vaccine.

The monoclonal antibody 4B11 (an IgM antibody) was bactericidal against strains 1000 and CU385. Note that the 4B11 monoclonal antibody did not react with these same strains by whole-cell ELISA at the highest concentration tested (see FIG. 19). The bactericidal assays measures functional antibody activity using live bacteria whereas the bacterial cell ELISA measures antibody binding to heat-killed bacteria, which in these strains may have denatured the antigenic target of mAb 4B11.

DEPOSITS

A deposit of biologically pure cultures of the materials in the table below was made with the American Type Culture Collection, 10801 University Blvd., Manassas, Va. 20110-2209, under the provisions of the Budapest Treaty, on or before the filing date of the present application. The accession number indicated is assigned after successful viability testing, and the requisite fees were paid. Access to said cultures will be available during pendency of the patent application to one determined by the Commissioner to be entitled to such under 37 C.F.R. §1.14 and 35 U.S.C. §122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

These deposits are provided merely as a convenience to those of skill in the art, and are not an admission that a deposit is required. A license may be required to make, use, or sell the deposited materials, and no such license is hereby granted. The deposit below was received by the ATCC on or before the filing date of the present application.

| Description | ATCC Accession No. |
| --- | --- |
| Hybridoma 1D9 | PTA-3552 |
| Hybridoma 4B11 | PTA-3553 |
| Hybridoma 9B8 | PTA-3551 |
| Hybridoma 14C7 | PTA-3554 |
| MenC strain RM1090 | PTA-3557 |
| MenB strain BZ198 | PTA-3555 |
| MenA strain Z1092 | PTA-3556 |

What is claimed is:

1. A method of eliciting an immune response against *Neisseria meningitidis*, said method comprising the steps of:
    administering to a mammal a first preparation comprising a first antigen composition from a first *Neisseria meningitidis* that is a member of a first serotype and of a first serosubtype, in an amount sufficient to elicit an immune response to epitopes present in said first antigen composition, wherein said first antigen composition comprises microvesicles (MV), outer membrane vesicles (OMV), or both OMV and MV; and
    administering to said mammal a second preparation comprising a second antigen composition from a second *Neisseria meningitidis* that is a member of a second serotype and of a second serosubtype, in an amount sufficient to elicit an immune response to epitopes present in said second antigen composition, wherein said second antigen composition comprises microvesicles (MV), outer membrane vesicles (OMV), or both OMV and MV;
    administering to said mammal a third preparation comprising a third antigen composition from a third *Neisseria meningitidis* that is a member of a third serotype and of a third serosubtype, in an amount sufficient to elicit an immune response to epitopes present in said third antigen composition, wherein said third antigen composition comprises microvesicles (MVs), outer membrane vesicles (OMVs), or both OMVs and MVs;
    wherein the *Neisseria meningitidis* of the first, second, and third preparations are of different serotypes,
    wherein said first, second, and third preparations are administered serially;
    wherein the second preparation is administered after said mammal has been immunologically primed by exposure to the first preparation, and the third preparation is administered after said mammal has been immunologically primed by exposure to the second preparation;
    wherein one or more of the first, second, and third preparations comprises aluminum phosphate or aluminum hydroxide; and
    wherein administering of the first, second, and third preparations is sufficient to elicit an immune response in said mammal, wherein said immune response confers protective immunity against more than one strain of *Neisseria meningitidis*.

2. The method of claim 1, wherein the first antigen composition comprises MVs, the second antigen composition comprises MVs, and the third antigen composition comprises OMVs.

3. The method of claim 1, wherein the mammal is a human.

4. A method of eliciting an immune response against serogroup B *Neisseria meningitidis*, said method comprising the steps of:
    administering to a mammal a first preparation comprising a first antigen composition from a first serogroup B *Neisseria meningitidis* that is a member of a first serosubtype, in an amount sufficient to elicit an immune response to epitopes present in said first antigen composition, wherein said first antigen composition comprises microvesicles (MV), outer membrane vesicles (OMV), or both OMV and MV;
    administering to said mammal a second preparation comprising a second antigen composition from a second serogroup B *Neisseria meningitidis* that is a member of a second serosubtype, in an amount sufficient to elicit an immune response to epitopes present in said second antigen composition, wherein said second antigen composition comprises microvesicles (MV), outer membrane vesicles (OMV), or both OMV and MV,
    wherein the serosubtype of each of the first and second serogroup B *Neisseria meningitidis* is different;

administering to said mammal a third preparation comprising a third antigen composition from a third serogroup B *Neisseria meningitidis* that is a member of a third serosubtype, the third antigen composition comprising outer membrane vesicles (OMV), MVs, or both OMVs and MVs, said administering being in an amount sufficient to elicit an immune response to epitopes present in said third antigen composition, wherein the serosubtype of at least the first and third serogroup B *Neisseria meningitidis* is different;

wherein said first, second, and third preparations are administered serially;

wherein the second preparation is administered after said mammal has been immunologically primed by exposure to the first preparation, and the third preparation is administered after said mammal has been immunologically primed by exposure to the second preparation;

wherein one or more of the first, second, and third preparations comprises aluminum phosphate or aluminum hydroxide; and wherein administering of the first, second, and third preparations is sufficient to elicit an immune response in said mammal, wherein said immune response confers protective immunity against more than one strain of serogroup B *Neisseria meningitidis*.

5. The method of claim 4, wherein the mammal is a human.

6. A method of eliciting an immune response against *Neisseria meningitidis*, said method comprising the steps of:

administering to a mammal a first preparation comprising a first antigen composition in an amount sufficient to elicit an immune response to epitopes present in said first antigen composition, wherein the first antigen composition comprises outer membrane vesicles (OMV) from a first *Neisseria meningitidis* strain expressing a first PorA protein, wherein the first antigen composition comprises the first PorA protein;

administering to the mammal a second preparation comprising a second antigen composition in an amount sufficient to elicit an immune response to epitopes present in said second antigen composition, wherein the second antigen composition comprises OMV from a second *Neisseria meningitidis* strain expressing a second PorA protein, wherein the PorA of the second *Neisseria meningitidis* strain is different from the PorA protein of the first *Neisseria meningitidis* strain, wherein the second antigen composition comprises the second PorA protein;

administering to said mammal a third preparation comprising a third antigen composition comprising OMV from a third *Neisseria meningitidis* strain expressing a third PorA protein, said administering being in an amount sufficient amount to elicit an immune response to epitopes present in said third antigen composition, wherein the PorA of the third *Neisseria meningitidis* strain is different from the PorA protein of the first and the second *Neisseria meningitidis* strains, and wherein the third antigen composition comprises the third PorA protein:

wherein said first, second, and third preparations are administered serially;

wherein the second preparation is administered after said mammal has been immunologically primed by exposure to the first preparation, and the third preparation is administered after said mammal has been immunologically primed by exposure to the second preparation;

wherein one or more of the first, second, and third preparations comprises aluminum phosphate or aluminum hydroxide; and wherein administering of the first, second, and third preparations elicits an immune response in said mammal, wherein said immune response confers protective immunity against more than one strain of *Neisseria meningitidis*.

7. The method of claim 6, wherein the mammal is a human.

\* \* \* \* \*

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
tccatgacgt tcctgacgtt                                              20
```